United States Patent
Hoppe-Seyler et al.

(10) Patent No.: US 11,931,349 B2
(45) Date of Patent: Mar. 19, 2024

(54) IRON CHELATORS IN TUMOR THERAPY

(71) Applicant: Deutsches Krebsforschungszentrum Stiftung des öffentlichen Rechts, Heidelberg (DE)

(72) Inventors: Felix Hoppe-Seyler, Hirschberg (DE); Julia A. Braun, Edingen-Neckarhausen (DE); Karin Hoppe-Seyler, Hirschberg (DE)

(73) Assignee: Deutsches Krebsforschungszentrum Stiftung des öffentlichen Rechts, Heidelberg (DE)

( * ) Notice: Subject to any disclaimer, the term of this patent is extended or adjusted under 35 U.S.C. 154(b) by 108 days.

(21) Appl. No.: 16/766,408

(22) PCT Filed: Nov. 23, 2018

(86) PCT No.: PCT/EP2018/082316
§ 371 (c)(1),
(2) Date: May 22, 2020

(87) PCT Pub. No.: WO2019/101897
PCT Pub. Date: May 31, 2019

(65) Prior Publication Data
US 2021/0369692 A1 Dec. 2, 2021

(30) Foreign Application Priority Data
Nov. 23, 2017 (EP) .................... 17203391

(51) Int. Cl.
| | |
|---|---|
| A61K 31/4418 | (2006.01) |
| A61K 31/16 | (2006.01) |
| A61K 31/345 | (2006.01) |
| A61K 31/4196 | (2006.01) |
| A61K 31/44 | (2006.01) |
| A61K 31/4412 | (2006.01) |
| A61K 31/444 | (2006.01) |
| A61K 45/06 | (2006.01) |
| A61P 35/00 | (2006.01) |

(52) U.S. Cl.
CPC .......... *A61K 31/4418* (2013.01); *A61K 31/16* (2013.01); *A61K 31/345* (2013.01); *A61K 31/4196* (2013.01); *A61K 31/44* (2013.01); *A61K 31/4412* (2013.01); *A61K 31/444* (2013.01); *A61K 45/06* (2013.01); *A61P 35/00* (2018.01)

(58) Field of Classification Search
None
See application file for complete search history.

(56) References Cited

U.S. PATENT DOCUMENTS

2014/0073645 A1* 3/2014 Linder ................... A61K 31/53
514/243
2015/0259349 A1* 9/2015 Linder ............... A61K 31/7076
514/243

OTHER PUBLICATIONS

Corce et al., Bioorganic & Medicinal Chemistry Letters (2016), 26(2), pp. 252-256.*
Simonart et al., Gynecologic Oncology (2002), 85(1), pp. 95-102.*
Tian et al., Cancer Letters (2010), 298, pp. 231-237.*
Tomat, Abstract, 68th Southwest Regional Meeting of the American Chemical Society, Baton Rouge, LA, Nov. 4-7, 2012, Meeting abstract pp. SWRM-164.*
Clement et al., "The Antifungal Drug Ciclopirox Inhibits Deoxyhypusine and Proline Hydroxylation, Endothelial Cell Growth and Angiogenesis In Vitro," Int J. Cancer, vol. 100, pp. 491-498, (2002).
De Martel et al., "Worldwide Burden of Cancer Attributable to HPV by Site, Country and HPV Type," Int. J Cancer, vol. 141, No. 4, pp. 664-670 (2017).
Dimri et al., A Biomarker that Identifies Senescent Human Cells in Culture and in Aging Skin in vivo, Proc. Natl. Acad. Sci., vol. 92, pp. 9363-9367 (1995).
Dyson et al., "The Human Papilloma Virus-16 E7 Oncoprotein Is Able to Bind to the Retinoblastoma Gene Product," Science, vol. 243, No. 4893, pp. 934-937 (1989).
Eberhard et al., "Chelation of Intracellular Iron with the Antifungal Agent Ciclopirox Olamine Induces Cell Death in Leukemia and Myeloma Cells," Blood, vol. 114, No. 14, pp. 3064-3073 (Oct. 2009).
Hall, et al., "RNA Interference of Human Papillomavirus Type 18 E6 and E7 Induces Senescence in Hela Cells," Journal of Virology, vol. 77, no. pp. 6066-6069 (May 2003).
Hill et al., "Hypoxia and Predicting Radiation Response," Seminars in Radiation Oncolology, vol. 25, No. 4, pp. 260-272 (2015).
Hoppe-Seyler et al., "Induction of Dormancy in Hypoxic Human Papillomavirus-Positive Cancer Cells," Proceedings of the National Academy of Sciences, vol. 114, No. 6, pp. E990-E998 (Jan. 2017).
Laberge et al., MTOR Regulates the Pro-Tumorigenic Senescene-Associated Secretory Phenotype by Promoting ILIA Translation, Nat. Cell Biol., vol. 17, No. 8, pp. 1049-1061 (Aug. 2015).
Fryknas et al: "Iron Chelators Target Both Proliferating and Quiescent Cancer Cells," Scientific Reports, vol. 6, No. 38343, 11 pages (Dec. 2016).
Martinez-Zapien et al., "Structure of the E6/E6AP/p53 Complex Required for HPV-Mediated Degradation of p53," Nature, vol. 529, No. 7587, pp. 541-545 (2016).

(Continued)

Primary Examiner — Brian J Davis
(74) Attorney, Agent, or Firm — Foley & Lardner LLP

(57) ABSTRACT

The present invention relates to a pharmaceutically compatible iron chelator or a prodrug thereof for use in treating and/or preventing cancer in a subject suspected or known to comprise hypoxic cancer cells, and use in treatment and/or prevention of a human papilloma virus (HPV) related lesion. The present invention further relates to a use of an iron chelator or prodrug thereof for inducing senescence in a cancer cell, preferably a hypoxic cancer cell; and to a method for inducing an irreversible proliferation arrest in cancer cells comprising a) contacting said cancer cells with an iron chelator or prodrug thereof and, thereby, b) inducing an irreversible proliferation arrest in said cancer cells.

9 Claims, 14 Drawing Sheets

(56) References Cited

OTHER PUBLICATIONS

Figure 1:
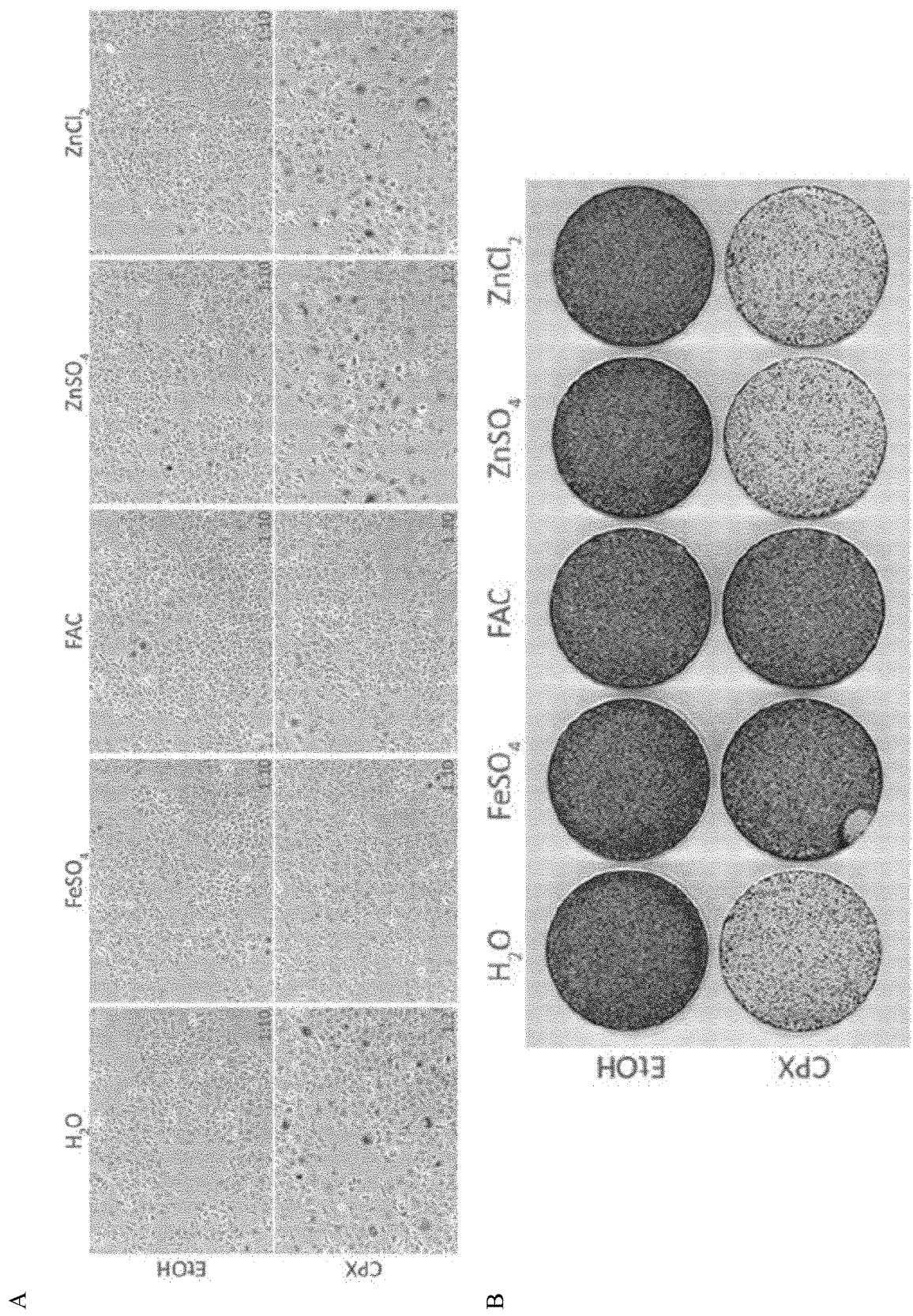

Khoshinani et al., "Hypoxia: A Double-Edged Sword in Cancer Therapy," *Cancer Investigation*, vol. 34, No. 10, pp. 536-545 (2016).
Overgaard, "Hypoxic Radiosensitization: Adored and Ignored," *Journal Clin Oncol*, vol. 25, No. 26, pp. 4066-4074 (Sep. 2007).
Sanvisens et al., "Function and Regulation of Yeast Ribonucleotide Reductase: Cell Cycle, Genotoxic Stress, and Iron Bioavailability," *Biomed J*, vol. 36, No. 2, pp. 51-58) (2013).
Shen Tao et al: "Abstract 3408: The anticancer mechanisms of ciclopirox olamine." *Cancer Research*, vol. 73, No. 8, Suppl 1, Apr. 2013.
Shen, et al., "Repositioning the Old Fungicide Ciclopirox for New Medical Uses," *Current Pharmaceutical Design*, vol. 22, No. 28, pp. 4443-4450 (2016).
Song et al., "Wnt Inhibitor Screen Reveals Iron Dependence of B-Catenin Signaling in Cancers," *Cancer Res.*, vol. 71, pp. 7628-7639, (Oct. 2011).
Torti, et al., "Iron and Cancer: More Ore to be Mined," *Nat Rev Cancer*, vol. 13, No. 5, pp. 342-355 (2013).
Vaupel et al., "Detection and Characterization of Tumor Hypoxia Using $pO_2$ Histography," *Antioxid Redox Signal*, 2007, 9(8): p. 1221-35 (2007).
Vaupel, et al., "Hypoxia in Cancer: Significance and Impact on Clinical Outcome," *Cancer Metastasis Rev*, vol. 26, No. 2, pp. 225-239 (2007).
Waris, et al., "Reactive Oxygen Species: Role in the Development of Cancer and Various Chronic Conditions," *Journal of Carcinogenesis*, vol. 5, No. 14, 8 pages (2006).
Weems Jessica et al: "Abstract 914: Cicloporox olamine (CPX) inhibits breast cancer cell proliferation by blocking the formation of a PEAK1-Src-eIF5a protein complex" *Cancer Research*, vol. 72, No. Suppl. 8 (Apr. 2012).
Zhou et al., "The Antitumor Activity of the Fungicide Ciclopirox," *Journal international du cancer*, vol. 127, No. 10, pp. 2467-2477 (2010).

* cited by examiner

A

B

A

B

IRON CHELATORS IN TUMOR THERAPY

This application is a U.S. National Stage of International Patent Application No. PCT/EP2018/082316, filed Nov. 23, 2018, which claims priority from European Patent Application No. 17203391.2, filed Nov. 23, 2017, all of which are incorporated herein by reference in their entirety.

The present invention relates to a pharmaceutically compatible iron chelator or a prodrug thereof for use in treating and/or preventing cancer in a subject suspected or known to comprise hypoxic cancer cells, and use in treatment and/or prevention of a human papillomavirus (HPV) related lesion. The present invention further relates to a use of an iron chelator or prodrug thereof for inducing senescence in a cancer cell, preferably a hypoxic cancer cell; and to a method for inducing an irreversible proliferation arrest in cancer cells comprising a) contacting said cancer cells with an iron chelator or prodrug thereof and, thereby, b) inducing an irreversible proliferation arrest in said cancer cells.

A common dogma of cancer physiology is that cancer cells exhibit higher intracellular iron levels than normal cells, which is believed to facilitate both initiation and growth of a tumor (Torti and Torti, Nat Rev Cancer, 2013, 13(5): p. 342-55). On the one hand, via the Fenton reaction, intracellular iron induces the production of reactive oxygen species and therefore increased iron levels can facilitate the initiation of a tumor (Waris and Ahsan, Journal of Carcinogenesis, 2006, 5: p. 14-14). On the other hand, cancer cells strongly depend on the activity of the iron dependent enzyme ribonucleotide reductase, which is necessary for DNA synthesis and thus proliferation (Sanvisens et al. Biomed J, 2013, 36(2): p. 51-8). Also, other iron-dependent enzymes have been implicated in the cancer-promoting effect of iron, e.g. Deoxyhypusine Hydroxylase (Clement et al., Int J. Cancer, 100: 491-498, 2002), or Wnt-Signaling (Song et al., Cancer Res. 71: 7628-7639, 2011).

Human Papillomaviruses (HPVs) are known to be associated with ca. 4.5% of all cancers worldwide (de Martel et al., Int J Cancer, 2017. 141(4): p. 664-670). Among these cancers are cancers of the cervix and other cancers within the anogenital region as well as head and neck cancers. The causative role of HPV is best characterized in cervical cancer. Two viral oncogenes, E6 and E7 are crucial for both the transformation of cells and the maintenance of the malignant phenotype. E7 binds to the tumor suppressor pRb and leads to the functional inhibition and degradation of pRb (Dyson et al., Science, 1989, 243(4893): p. 934-7). Thereby the transcriptional activator E2F is liberated and can trigger cell cycle progression into S phase. When E7 alone is expressed in cells, p53 is induced and cells undergo apoptosis. However, when E6 is additionally expressed, a tumor can form, because E6 forms a complex with E6AP and p53 and induces the degradation of p53, thereby blocking apoptosis (Martinez-Zapien et al., Nature, 2016, 529(7587): p. 541-5.). If E6/E7 are repressed (e.g., via siRNA) under standard cell culture conditions, the cells rapidly undergo senescence (Hall and Alexander, J Virol, 2003, 77(10): p. 6066-9). However, these conditions do not reflect the conditions present in the body. E.g., in normal cervix tissue, there is a median oxygen concentration of 5.5% (physoxia).

In tumors, frequently very low oxygen concentrations are present due to abnormalities of tumor microvasculature and diffusion limitations; e.g. in cervical cancer, the median oxygen concentration is about 1.2% (Vaupel et al., Antioxid Redox Signal, 2007, 9(8): p. 1221-35; Vaupel and Mayer, Cancer Metastasis Rev, 2007, 26(2): p. 225-39). Notably, although in hypoxic areas of cervical cancer E6 and E7 are repressed (Hoppe-Seyler et al., Proceedings of the National Academy of Sciences, 2017, 114(6): p. E990-E998), cancer cells do not undergo efficient senescence, since the mTOR pathway necessary for senescence is impaired. Another obstacle in targeting hypoxic areas of cancer is that the resistance of cancer cells towards chemotherapy (CT) or radiotherapy (RT) increases with decreasing oxygen concentrations (Overgaard J Clin Oncol, 2007, 25(26): p. 4066-74; Hili et al., Sem in Radial Oncol, 2015, 25(4):p. 260-72; Manoochehri Khoshinani et al., Cancer Invest, 2016, 34(10): p. 536-545). Thus, efficient CT and RT are limited to tumor sections with good oxygen supply.

Ciclopirox (CPX) is clinically used as a topical antifungal agent to treat mycoses of the skin and nails. Although its exact mechanism of action is unclear, it is known to chelate intracellular iron (Shen and Huang, Curr Pharm Des, 2016, 22(28): p. 4443-50) and anti-tumor properties have been reported (Zhou et al., Journal international du cancer, 2010, 127(10): p. 2467-2477; Eberhard et al., Blood, 2009, 114 (14): p. 3064-3073).

There is, thus, a need in the art for improved methods for treating tumors, in particular tumors having hypoxic sections in which chemotherapy and radiotherapy are ineffective. It is therefore an objective of the present invention to provide means and methods to comply with the aforementioned needs, avoiding at least in part the disadvantages of the prior art. This problem is solved by compounds and the methods, kits and uses of the present invention. Embodiments, which might be realized in an isolated fashion or in any arbitrary combination, are listed in the dependent claims.

Accordingly, the present invention relates to a pharmaceutically compatible iron chelator for use in treating and/or preventing cancer in a subject suspected or known to comprise hypoxic cancer cells.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, as used in the following, the terms "preferably", "more preferably", "most preferably", "particularly", "more particularly", "specifically", "more specifically" or similar terms are used in conjunction with optional features, without restricting further possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding further embodiments of the invention, without any restrictions regarding the scope of the invention and without any restriction regarding the possibility of combining the features introduced in such way with other optional or non-optional features of the invention.

As used herein, the term "standard conditions", if not otherwise noted, relates to IUPAC standard ambient temperature and pressure (SATP) conditions, i.e. preferably, a temperature of 25° C. and an absolute pressure of 100 kPa; also preferably, standard conditions include a pH of 7. Moreover, if not otherwise indicated, the term "about" relates to the indicated value with the commonly accepted technical precision in the relevant field, preferably relates to the indicated value ±20%, more preferably ±10%, most preferably ±5%. Further, the term "essentially" indicates that deviations having influence on the indicated result or use are absent, i.e. potential deviations do not cause the indicated result to deviate by more than ±20%, more preferably ±10%, most preferably ±5%. Thus, "consisting essentially of" means including the components specified but excluding other components except for materials present as impurities, unavoidable materials present as a result of processes used to provide the components, and components added for a purpose other than achieving the technical effect of the invention. For example, a composition defined using the phrase "consisting essentially of" encompasses any known acceptable additive, excipient, diluent, carrier, and the like. Preferably, a composition consisting essentially of a set of components will comprise less than 5% by weight, more preferably less than 3% by weight, even more preferably less than 10%, most preferably less than 0.10% by weight of non-specified component(s).

As used herein, the term "iron chelator" relates to a chemical compound forming a stable complex with iron ions, preferably $Fe^{2+}$ and/or $Fe^{3+}$. Preferably, the iron chelator is a compound having a log stability constant for at least one of its iron complexes of at least 3, more preferably at least 5, more preferably 10, still more preferably at least 20, even more preferably at least 25, most preferably at least 30. Preferably, the log stability constant is the log of the equilibrium constant for the formation of the Fe/iron chelator complex in aqueous solution, preferably determined under standard conditions, preferably as specified elsewhere herein; preferably, the log stability constant of an iron chelator is determined in a solution consisting of water, iron ions, and iron chelator. Iron chelators are, in principle, known in the art and include compounds comprising at least one of a 2-pyridone structure, a hydroxamate structure, a (thio)semicarbazone structure, a bis(2-hydroxyphenyl)-1H-1,2,4-triazol structure, an alpha-hydroxyketone structure, an arylhydrazone structure, and a catechol structure.

The term "pharmaceutically compatible", as used herein, relates to a chemical compound which is pharmaceutically acceptable in the sense of being not deleterious to the recipient thereof and, preferably, being compatible with optional other ingredients of a formulation thereof. Preferably, a pharmaceutically compatible compound is a compound causing at most moderate adverse drug reactions, preferably causing at most mild adverse drug reactions. As used herein, the term "mild" adverse reactions relates to adverse reactions not requiring medical intervention, such as skin rashes, headaches, digestive disturbances, fatigue, and the like; "moderate" adverse reactions are adverse reactions requiring medical intervention, but not being potentially life threatening.

In accordance, a "pharmaceutically compatible iron chelator" is an iron chelator as specified herein above which is pharmaceutically compatible as specified above. Thus, preferably, the pharmaceutically compatible iron chelator is an iron chelator comprising a chemical compound in clinical use, preferably approved for clinical use by at least one of the Food and Drug Administration (FDA), the European Medicines Agency (EMEA), and the Bundesinstitut für Arzneimittel und Medizinprodukte (BfArM). More preferably, the pharmaceutically compatible iron chelator is an iron chelator comprising a chemical compound in clinical use as an iron chelator, preferably approved for clinical use by at least one of the aforesaid institutions. Thus, preferably, the iron chelator is ciclopirox (2(1H)-Pyridinone, 6-cyclohexyl-1-hydroxy-4-methylpyridin-2(1H)-one; CAS-No: 29342-05-0), Deferoxamine (DFO, CAS No. 70-51-9) or hydroxycarbamide (CAS No. 127-07-1, nitrofural (CAS No. 59-87-0), 3-aminopyridine-2-carboxaldehyde Thiosemicarbazone (Triapine, CAS No. 236392-56-6) or 5-Hydroxy-pyridine-2-carboxaldehyde Thiosemicarbazone (HPCT, CAS No. 19494-89-4), Deferasirox (CAS No. 201530-41-8), iv) Deferiprone (Cas No. 30652-11-0), or N,N'N''-tris(2-pyridylmethyl)-cis,cis-1,3,5-triaminocyclohexane (Tachpyr).

Preferably, the pharmaceutically compatible iron chelator is a 2-pyridone derivative and/or a prodrug thereof.

The term "prodrug" is understood by the skilled person to relate to a compound not having or having only to a reduced extent the relevant activity of being an iron chelator and being converted in the body of a subject to the actual active compound. Thus, preferably, a prodrug is an ether or preferably an ester of the iron chelator. More preferably, the prodrug is a glycosylate, a phosphate, a sulphate, or a macromolecule-conjugated, e.g. polyethyleneglycol (PEG) conjugated, derivative of the iron chelator.

The term "2-pyridone derivative", as used herein, relates to a compound comprising, at least in a tautomeric form, a Pyridin-2(1H)-one structure. More preferably, the 2-pyridone derivative is a chemical compound comprising a 1-Hydroxy-Pyridin-2(1H)-one structure. More preferably, the 2-pyridone derivative is a compound comprising structure (I)

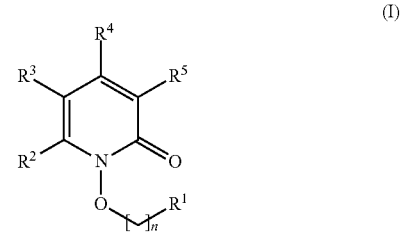

(I)

with n being 0, 1, 2, 3, 4, 5, or 6;

$R^1$ being H, an optionally substituted carbonyl, optionally substituted phosphoryl, or optionally substituted sulfonyl;

$R^2$ to $R^5$ being independently selected from —H, an optionally substituted organic side chain, and halogen.

The term "side chain" is understood by the skilled person and relates to an atom or chemical group attached covalently to the core part of a chemical compound as described herein, said core part also being referred to as "main chain" or "backbone". Preferably, the side chain is an organic side chain as described herein below. The term "substituted" side chain relates to a side chain substituted at one or more positions, preferably, at 1, 2, or 3 positions, wherein substituents may be attached at any available atom to produce a stable chemical compound. It is understood by the skilled person that the term "optionally substituted" side chain relates to an unsubstituted or to a substituted side chain.

The term "organic side chain", as used herein, relates to any, optionally substituted, side chain comprising at least one carbon atom. Preferably, the organic side chain is an, optionally substituted, alkyl, alkenyl, alkinyl, aryl, aralkyl, cycloalkyl, heterocycloalkyl, or heteroaryl side chain. Preferably, a substituted organic side chain is an organic side chain substituted with at least one substituent independently selected from —COO—, =O, —OH, —CN, halogen, —$NH_2$, —NH(alkyl), —N(alkyl)$_2$, —N(alkyl)$_3$%, —NH (aryl), N(aryl)$_2$, —$NO_2$, —O(alkyl), —O—$(CH_2)$n-OH, —O—$(CH_2)$n-O(alkyl), —O(aralkyl), —O(aryl), —$OPO_3^{2-}$, —$PO_3^{2-}$, —$OSO_3^-$ and —$SO_3^-$. Preferably, the alkyl, aryl, and aralkyl groups of the substituents are not further substituted by groups comprising alkyl, alkenyl, alkinyl, aryl, aralkyl, heterocycloalkyl, or heteroaryl groups. More preferably, the alkyl, aryl, and aralkyl groups of the substituents are not further substituted.

The term "alkyl", as used herein, relates to a straight or branched chain, saturated hydrocarbon group, linked to the main chain by a covalent bond to at least one of its at least one carbon atoms. Preferred alkyl groups are straight chain alkyls, e.g., preferably, methyl, ethyl, propyl, butyl, pentyl, hexyl, or branched chain alkyl groups, e.g., preferably, —$CH(CH_3)_2$, —$CH(CH_2CH_3)_2$, —$C(CH_3)_3$, —$C(CH_2CH_3)_3$, —$CH(CH_3)(CH_2CH_3)$, —$CH_2CH(CH_3)_2$, —$CH_2CH(CH_3)(CH_2CH_3)$, —$CH_2CH(CH_2CH_3)_2$, —$CH_2C(CH_3)_3$, —$CH_2C(CH_2CH_3)_3$, —$CH(CH_3)CH(CH_3)(CH_2CH_3)$, —$CH_2CH_2CH(CH_3)_2$, —$CH_2CH_2CH(CH_3)(CH_2CH_3)$, —$CH_2CH_2CH(CH_2CH_3)_2$, —$CH_2CH_2C(CH_3)_3$, —$CH_2CH_2C(CH_2CH_3)_3$, —$CH(CH_3)CH_2CH(CH_3)_2$, or —$CH(CH_3)CH(CH_3)CH(CH_3)_2$.

Accordingly, alkyl groups include primary alkyl groups, secondary alkyl groups, and tertiary alkyl groups. The term "cycloalkyl" relates to a circularly closed, hydrocarbon group, preferably with 5 to 8 carbon atoms. Preferred cycloalkyls are cyclopentyl, cyclohexyl, cycloheptyl, and cyclooctyl.

The term "alkenyl" side chain relates to a side chain comprising at least one C=C double bond and linked to the main chain by a covalent bond to at least one of its at least two carbon atoms. Accordingly, the term "alkinyl" side chain relates to a side chain comprising at least one C≡C triple bond linked to the main chain by a covalent bond to at least one of its at least two carbon atoms.

The term "cycloalkenyl" relates to a circularly closed hydrocarbon group, preferably with 5 to 12 carbon atoms, comprising at least one C=C double bond and linked to the main chain by a covalent bond to at least one of its at least two carbon atoms. The term "cycloalkinyl" relates to a circularly closed hydrocarbon group, preferably with 8 to 12 carbon atoms, comprising at least one C≡C triple bond and linked to the main chain by a covalent bond to at least one of its at least two carbon atoms.

As used herein, the term "alkoxy" side chain relates to an —O-alkyl side chain, preferably having the indicated number of carbon atoms. Preferably, the alkoxy side chain is —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, or —O-neohexyl.

The term "aryl", as used herein, relates to an aromatic ring or ring system having 6 to 14 carbon atoms, preferably comprising one, two, or three aromatic rings. Preferred aryl side chains are phenyl, naphthyl, anthracenyl, and phenanthrenyl. The term "ring", in the context of the chemical compounds of the present invention, is understood by the skilled person; accordingly, the term "ring system" relates to a chemical structure comprising at least two rings sharing at least one covalent bond. Thus, preferably, "aryl" also includes aromatic ring systems fused with a cycloalkyl and/or a heterocycloalkyl ring.

As used herein, the tem "aralkyl" relates to an alkyl side chain, wherein at least one hydrogen is replaced by an aryl side chain. Preferably, aralkyl is benzyl or phenethyl.

The term "heterocycloalkyl", as used herein, relates to a saturated or partially unsaturated ring or ring system having 5 to 14 ring atoms, preferably 5 to 7 ring atoms, wherein at least one ring atom is a heteroatom selected from the group consisting of N, O, and S, said ring or ring system being linked to the main chain by a covalent bond to a C or N atom of said ring or ring system. Preferably, heterocycloalkyl is azepinyl, dihydrofuryl, dihydropyranyl, imidazolidinyl, imidazolinyl, isothiazolidinyl, isoxazolidinyl, morpholinyl, oxazolidinyl, piperazinyl, piperidinyl, pyrazolidinyl, pyrrolidinyl, tetrahydrofuryl, tetrahydropyranyl, thiadiazolylidinyl, thiazolidinyl, or thiomorpholinyl.

As used herein, the term "heteroaryl" relates to an aromatic ring or ring system having 5 to 14 ring atoms, preferably 5 to 7 ring atoms, wherein at least one ring atom is a heteroatom selected from the group consisting of N, O, and S, said ring or ring system being linked to the main chain by a covalent bond to a C or N atom of said ring or ring system. Preferably, up to 4, more preferably up to 3, most preferably up to 2 ring atoms per ring are heteroatoms independently selected from the group of heteroatoms consisting of N, O, and S. Preferably, heteroaryl is pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, or indolyl.

More preferably, the pharmaceutically compatible iron chelator is a compound comprising structure (I), with n being 0, 1, 2, 3, 4, 5, or 6; $R^1$ being H, an optionally substituted carbonyl, optionally substituted phosphoryl, or optionally substituted sulfonyl; and $R^2$ to $R^5$ being independently selected from —H, alkyl, alkenyl, cycloalkyl, cycloalkenyl, alkoxy, aryl aralkyl, heterocycloalkyl, heteroaryl, and halogen.

Still more preferably, the pharmaceutically compatible iron chelator is a compound comprising structure (I), with n being 0, 1, 2, 3, 4, 5, or 6; $R^1$ being H, optionally substituted carbonyl, optionally substituted phosphoryl, or optionally substituted sulfonyl; $R^2$ being selected from cyclohexyl, —H, $C_1$-$C_6$ alkyl, $C_5$-$C_8$ cycloalkyl, $C_1$-$C_6$ alkoxy, and halogen; $R^4$ being selected from methyl, —H, $C_1$-$C_6$ alkyl, $C_5$-$C_8$ cycloalkyl, $C_1$-$C_6$ alkoxy, and halogen; and $R^3$ and $R^5$ being independently selected from —H, $C_1$-$C_6$ alkyl, $C_5$-$C_8$ cycloalkyl, $C_1$-$C_6$ alkoxy, and halogen.

Most preferably, the pharmaceutically compatible iron chelator is a compound comprising structure (I), wherein n=0, $R^1$ is H, optionally substituted carbonyl, or optionally substituted phosphoryl; $R^2$ is cyclohexyl; $R^4$ is methyl; and $R^3$ and $R^5$ are —H; i.e. preferably, the pharmaceutically compatible iron chelator is ciclopirox (2(1H)-Pyridinone, 6-cyclohexyl-1-hydroxy-4-methylpyridin-2(1H)-one; CAS-No: 29342-05-0), preferably ciclopirox olamine.

The terms "treating" and "treatment" refer to an amelioration of the diseases or disorders referred to herein or the symptoms accompanied therewith to a significant extent. Said treating as used herein also includes an entire restoration of health with respect to the diseases or disorders referred to herein. It is to be understood that treating, as the term is used herein, may not be effective in all subjects to be treated. However, the term shall require that, preferably, a statistically significant portion of subjects suffering from a disease or disorder referred to herein can be successfully treated. Whether a portion is statistically significant can be determined without further ado by the person skilled in the art using various well known statistic evaluation tools, e.g., determination of confidence intervals, p-value determination, Student's t-test, Mann-Whitney test etc. Preferred confidence intervals are at least 90%, at least 95%, at least 97%, at least 98% or at least 99%. The p-values are, preferably, 0.1, 0.05, 0.01, 0.005, or 0.0001. Preferably, the treatment shall be effective for at least 10%, at least 20% at least 50% at least 60%, at least 70%, at least 80%, or at least 90% of the subjects of a given cohort or population. Preferably, treating cancer is reducing tumor burden in a subject. As will be understood by the skilled person, effectiveness of treatment of e.g. cancer is dependent on a variety of factors including, e.g. cancer stage and cancer type. Preferably, treating causes inappropriately proliferating cells, preferably neoplastic cells, more preferably cancer cells, to enter into an irreversible proliferation arrest as specified elsewhere herein, preferably senescence. Thus, preferably, treating has the effect of causing a tumor to stop growing, more preferably to cause regression of a tumor, more preferably of causing a tumor to resolve. As used herein, the above relates to treating a HPV-related lesion mutatis mutandis.

The tem "preventing" refers to retaining health with respect to the diseases or disorders referred to herein for a certain period of time in a subject. It will be understood that the said period of time may be dependent on the amount of the drug compound which has been administered and individual factors of the subject discussed elsewhere in this specification. It is to be understood that prevention may not be effective in all subjects treated with the compound according to the present invention. However, the term requires that, preferably, a statistically significant portion of subjects of a cohort or population are effectively prevented from suffering from a disease or disorder referred to herein or its accompanying symptoms. Preferably, a cohort or population of subjects is envisaged in this context which normally, i.e. without preventive measures according to the present invention, would develop a disease or disorder as referred to herein. Whether a portion is statistically significant can be determined without further ado by the person skilled in the art using various well known statistic evaluation tools discussed elsewhere in this specification. As used herein, the above relates to preventing a HPV-related lesion mutatis mutandis.

Preferably, treating and/or preventing comprises topical application of the pharmaceutically compatible iron chelator, preferably to a mucosa and/or a skin. More preferably, treatment comprises topical application of said pharmaceutically compatible iron chelator to a hypoxic zone of a tumor, preferably including penetration of the iron chelator into a hypoxic zone of a tumor. Also preferably, treating and/or preventing cancer comprises inducing an irreversible proliferation arrest in a hypoxic cancer cell, which may, preferably, proceed to cell death, in particular apoptosis, under prolonged treatment and/or increased dose of iron chelator. The term "irreversible proliferation arrest", as used herein, relates to all states of a cell in which no further cell division occurs. Preferably, the irreversible proliferation arrest is a cell death mechanism and/or senescence, more preferably is senescence, in a preferred embodiment is apoptosis. Cell death mechanisms are known to the skilled person and include in particular apoptosis, mitotic catastrophe, autophagy, and necrosis. Senescence is the phenomenon of a diploid cell ceasing to divide, although, preferably, a senescent cell may remain metabolically active over a period of days or weeks. Preferably, a senescent cell can be identified by the absence of molecular proliferation markers and/or by the presence of senescence markers; preferred senescence markers are those described herein in the examples. Preferably, in a population of cells under an irreversible proliferation arrest, less than 1%, more preferably less than 0.1%, most preferably less than 0.01% of cells re-enter proliferation even upon incubation under conditions suitable for proliferation. As used herein, the above relates to treating and/or preventing a HPV-related lesion mutatis mutandis.

The term "inappropriate cellular proliferation" relates to an abnormal proliferation of body cells in a subject; as a consequence, an imbalance of cellular composition of a body tissue, of a body fluid and/or tumor formation may ensue. Inappropriate cellular proliferation may be induced by an infectious agent, preferably a virus, more preferably an oncogenic virus, more preferably Epstein-Barr virus, a hepatitis virus, Human T-lymphotropic virus 1, a papillomavirus, Human herpesvirus 8, most preferably a human papillomavirus (HPV). Inappropriate cellular proliferations may, however, also be induced by chemical compounds, e.g. a carcinogen, or endogenously, e.g. caused by spontaneous mutation. Preferably, inappropriate cellular proliferation is benign, i.e. preferably, does not threaten health or life of a subject. Preferred benign inappropriate cellular proliferations are warts, exophytic growing papillomas, condylomata, inverted papillomas, and pre-neoplastic HPV-induced lesions. More preferably, inappropriate cellular proliferation is malignant, i.e. does threaten health or life of a subject; thus, preferably, the malignant inappropriate cellular proliferation is cancer. The term "cancer", as used herein, relates to a disease of an animal, including man, characterized by uncontrolled growth by a group of body cells ("cancer cells"). This uncontrolled growth may be accompanied by intrusion into and destruction of surrounding tissue and possibly spread of cancer cells to other locations in the body. Preferably, also included by the term cancer is a relapse. Thus, preferably, the cancer is a solid cancer, a metastasis, or a relapse thereof.

Preferably, the cancer is selected from the list consisting of acute lymphoblastic leukemia, acute myeloid leukemia, adrenocortical carcinoma, aids-related lymphoma, anal cancer, appendix cancer, astrocytoma, atypical teratoid, basal cell carcinoma, bile duct cancer, bladder cancer, brain stem glioma, breast cancer, burkitt lymphoma, carcinoid tumor, cerebellar astrocytoma, cervical cancer, chordoma, chronic lymphocytic leukemia, chronic myelogenous leukemia, colon cancer, colorectal cancer, craniopharyngioma, endometrial cancer, ependymoblastoma, ependymoma, esophageal cancer, extracranial germ cell tumor, extragonadal germ cell tumor, extrahepatic bile duct cancer, fibrosarcoma, gallbladder cancer, gastric cancer, gastrointestinal stromal tumor, gestational trophoblastic tumor, hairy cell leukemia, head and neck cancer, hepatocellular cancer, hodgkin lymphoma, hypopharyngeal cancer, hypothalamic and visual pathway glioma, intraocular melanoma, kaposi sarcoma, laryngeal cancer, medulloblastoma, medulloepithelioma, melanoma, merkel cell carcinoma, mesothelioma, mouth cancer, multiple endocrine neoplasia syndrome, multiple myeloma, mycosis fungoides, nasal cavity and paranasal sinus cancer, nasopharyngeal cancer, neuroblastoma, non-hodgkin lymphoma, non-small cell lung cancer, oral cancer, oropharyngeal cancer, osteosarcoma, ovarian cancer, ovarian epithelial cancer, ovarian germ cell tumor, ovarian low malignant potential tumor, pancreatic cancer, papillomatosis, paranasal sinus and nasal cavity cancer, parathyroid cancer, penile cancer, pharyngeal cancer, pheochromocytoma, pituitary tumor, pleuropulmonary blastoma, primary central nervous system lymphoma, prostate cancer, rectal cancer, renal cell cancer, retinoblastoma, rhabdomyosarcoma, salivary gland cancer, sézary syndrome, small cell lung cancer, small intestine cancer, soft tissue sarcoma, squamous cell carcinoma, squamous neck cancer, testicular cancer, throat cancer, thymic carcinoma, thymoma, thyroid cancer, urethral cancer, uterine sarcoma, vaginal cancer, vulvar cancer, waldenström macroglobulinemia, and wilms tumor. More preferably, the cancer is a solid cancer, a metastasis, or a relapse thereof. Most preferably, the cancer is a tumor of a HPV-positive cancer, preferably HPV-positive head and neck cancer and/or cervix carcinoma. Thus, preferably, the cancer cells are papillomavirus-positive cancer cells, preferably are human papillomavirus-positive cancer cells. As specified herein below, more preferably, the cancer cells are papillomavirus-positive hypoxic cancer cells, preferably are human papillomavirus-positive hypoxic cancer cells. Preferably, the hypoxic cancer cells are slowly proliferating or non-dividing hypoxic cancer cells, the term "slowly proliferating" relating to cancer cells having an average doubling time of at least 1 week, preferably at least 2 weeks, more preferably more than one month, still more preferably at least 2 months, most preferably at least 4 months.

The term "subject", as used herein, relates to an animal, preferably a vertebrate, more preferably a mammal, in particular to livestock like cattle, horse, pig, sheep, and goat, or to a laboratory animal like a rat, mouse, and guinea pig. Most preferably, the subject is a human.

The terms "hypoxic" and "hypoxia" are understood by the skilled person to relate to a reduced oxygen tension compared to oxygen tension in normal air under standard pressure. Preferably, the term includes absence of oxygen (anoxia). Preferably, a hypoxic condition (hypoxia) is an oxygen tension of at most 40 mmHg, preferably at most 20 mmHg, more preferably at most 7.5 mmHg. Also preferably, a hypoxic condition (hypoxia) is an oxygen saturation of at most 5%, preferably at most 3%, more preferably at most 1%. Correspondingly, the term "hypoxic cancer cell", as used herein, relates to a cancer cell existing or maintained under hypoxia as specified above. Thus, hypoxic cancer cells are cells under an oxygen tension of at most 40 mmHg, preferably at most 20 mmHg, more preferably at most 7.5 mmHg. Also preferably, hypoxic cancer cells are cells under an oxygen saturation of at most 5%, preferably at most 3%, more preferably at most 1%. As will be understood by the skilled person, in a living tissue perfused by blood, i.e. preferably, in situ in a subject, oxygen supply may also be determined by determining oxygen saturation of hemoglobin, e.g. by diffuse optical spectroscopic imaging with near infrared light. Thus, preferably, hypoxic cancer cells are cells in a tissue, in particular in a tumor, in which the oxygen saturation of hemoglobin is less than 75%, more preferably less than 50%, most preferably less than 40%. As is known to the skilled person, tumors, in particular malignant tumors, quickly outgrow their blood supply, leaving at least parts of the tumor under hypoxic conditions. Thus, as used herein, hypoxic cancer cells are cells comprised in a tumor mass having a diameter of at least 1 mm, preferably at least 5 mm, more preferably at least 10 mm, even more preferably at least 2 cm, most preferably at least 5 cm. Thus, as used herein, a subject comprising a tumor having at least a size as indicated is a subject suspected to comprise hypoxic cancer cells. Further, methods for assessing oxygen tension and/or oxygen saturation, in particular oxygen saturation of hemoglobin, are known in the art; thus, a subject comprising at least one tumor for which it is determined that it comprises at least one section having hypoxic conditions, is a subject known to comprise hypoxic cancer cells.

Preferably, treating and/or preventing cancer comprises administration of at least one further anticancer therapy, preferably selected from radiotherapy, chemotherapy, anti-hormone therapy, targeted therapy, immunotherapy, and any combination thereof. More preferably, treating and/or preventing cancer comprises administration of chemotherapy, radiotherapy, or radio-chemotherapy. Preferably, the anticancer therapy comprises activation of mammalian target of rapamycin (mTOR) signaling; in a preferred embodiment, mTOR is mammalian target of rapamycin complex 1 (mTORC1). Also preferably, treating and/or preventing cancer further comprises abstaining from iron repletion measures, preferably abstaining from transfusion of blood or a blood product and/or of administration of iron-providing compounds. Preferably, treating and/or preventing cancer further comprises administering iron depletion therapy; preferably, the compound administered for iron depletion therapy is different from the pharmaceutically compatible iron chelator as specified herein. More preferably, the compound administered for iron depletion therapy is a pharmaceutically compatible iron chelator as specified herein. Most preferably, the same pharmaceutically compatible iron chelator is used for treating and/or preventing cancer and for iron depletion therapy. As used herein, the above relates to treating and/or preventing a HPV-related lesion mutatis mutandis.

As used herein, the term "chemotherapy" relates to treatment of a subject with an antineoplastic drug. Preferably, chemotherapy is a treatment including alkylating agents (e.g. cyclophosphamide), platinum (e.g. carboplatin), antimetabolites (e.g. 5-Fluorouracil), anthracyclines (e.g. doxorubicin, epirubicin, idarubicin, or daunorubicin), topoisomerase II inhibitors (e.g. etoposide, irinotecan, topotecan, camptothecin, or VP16), anaplastic lymphoma kinase (ALK)-inhibitors (e.g. Crizotinib or AP26130), aurora kinase inhibitors (e.g. N-[4-[4-(4-Methylpiperazin-1-yl)-6-[(5-methyl-1H-pyrazol-3-yl)amino]pyrimidin-2-yl]sulfanylphenyl]cyclopropanecarboxamide (VX-680)), or Iodine131-1-(3-iodobenzyl)guanidine (therapeutic metaiodobenzylguanidine), or histone deacetylase (HDAC) inhibitors, alone or any suitable combination thereof. It is to be understood that chemotherapy, preferably, relates to a complete cycle of treatment, i.e. a series of several (e.g. four, six, or eight) doses of antineoplastic drug or drugs applied to a subject, which may be separated by several days or weeks without such application.

The terms "radiation therapy" and "radiotherapy" are known to the skilled artisan. The term relates to the use of ionizing radiation to treat or control cancer.

The term "targeted therapy", as used herein, relates to application to a patient a chemical substance known to block growth of cancer cells by interfering with specific molecules known to be necessary for tumorigenesis or cancer or cancer cell growth. Examples known to the skilled artisan are small molecules like, e.g. PARP-inhibitors (e.g. Iniparib), antiangiogenic agents (e.g. Bevacizumab, Ramucirumab, Ziv-aflibercept), signalling inhibitors (e.g. cetuximab or panitumumab), or kinase inhibitors (e.g. Regorafenib).

The term "immunotherapy" as used herein relates to the treatment of cancer by modulation of the immune response of a subject. Said modulation may be inducing, enhancing, or suppressing said immune response, e.g. by administration of at least one cytokine, and/or of at least one antibody specifically recognizing cancer cells. The term "cell based immunotherapy" relates to a cancer therapy comprising application of immune cells, e.g. T-cells, preferably tumor-specific NK cells, to a subject.

Preferably, treating and/or preventing cancer is treating and/or preventing HPV-related cancer. Preferably, said treating and/or preventing further comprises inhibition of expression of an HPV E6 gene and/or E7 gene in HPV-positive cells. Preferably, expression of an HPV E6 gene and/or E7 gene is inhibited by administration of the pharmaceutically compatible iron chelator as specified elsewhere herein.

Advantageously, it was found that iron chelators cause cancer cells to enter senescence and that this senescence induction is independent of the mTOR pathway. Preferably, iron chelators cause cancer cells to enter apoptosis under hypoxic conditions. Thus, in contrast to conventional therapy, senescence can be induced by an iron chelator also under hypoxic conditions, under which mTOR is not available, and/or, preferably, apoptosis can be induced under hypoxic conditions, where chemotherapy and radiotherapy are inefficient. Thus, the iron chelator as specified herein enables therapy of cancer cells which would otherwise escape treatment.

The definitions made above apply mutatis mutandis to the following. Additional definitions and explanations made further below also apply for all embodiments described in this specification mutatis mutandis.

The present invention further relates to a pharmaceutically compatible iron chelator for use in treatment and/or prevention of a human papillomavirus (HPV) related lesion.

As used herein, the term "papillomavirus" (PV) relates to a DNA virus from the papillomaviridae family of viruses that infects the skin and mucous membranes of mammals, preferably livestock, more preferably cattle and horses, most preferably humans. For human PV (HPV), more than 110 HPV genotypes have been described (de Villiers, E. M., C. Fauquet, T. R. Broker, H. U. Bernard, and H. zur Hausen. 2004. Classification of papillomaviruses. Virology 324:17-27). Approximately 50 HPV genotypes are known to infect the mucosa. These mucosal genotypes are classified into three different groups based on their epidemiological association with cancer: "low-risk" human papillomaviruses (LR-HPV), "high-risk" human papillomaviruses (HR-HPV) and "putative high-risk" human papillomaviruses (pHR-HPV). It is also known that HR-HPVs can cause vulvar, anal, vaginal, penile, and oropharyngeal cancer, as well as vaginal intraepithelial neoplasia, anal intraepithelial neoplasia, vulvar intraepithelial neoplasia, and penile intraepithelial neoplasia. Preferably, HPVs are mucosal HPVs; more preferably, HPVs of the current invention are High-risk HPV genotypes (HR-HPVs), which are the main cause for the development of cervical cancer. Preferably, the HPV is at least one of HPV 31, 33, 35, 39, 45, 51, 52, 56, 58, 59, 68, 73 and 82, more preferably at least on of HPV 6, 16, 18, 31, 33, 35, 39, 45, 51, 56, 59 and 82, most preferably at least one of HPV 6, 16, 18, 31, 33, 35, 51 and 59.

The term "HPV related lesion" is known to the skilled person and relates to a benign or malignant tumor associated with the presence of at least one HPV genotype in at least part of the tumor cells. Preferably, the HPV related lesion is selected from the group consisting of warts, exophytic growing papillomas, condylomata, inverted papillomas, pre-neoplastic HPV-induced lesions, and neoplastic HPV-induced lesions. More preferably, the HPV-related lesion is a neoplastic HPV-related lesion selected from the list consisting of cervical neoplasia, rectal neoplasia, neoplasia of the anal epithelium, neoplasia of the oropharynx, and neoplasia of the tonsils.

Preferably, the pharmaceutically compatible iron chelator is provided on a polymer carrier comprising at least one of cotton, cellulose, dextran, polyethylene, polypropylene, poly(dimethylsiloxane), ethylene vinyl acetate copolymers, polycarophil, hydroxypropyl methylcellulose and polyacrylic acids. Preferably, the polymer carrier is a cervical cap, a swab, a tampon, a vaginal ring, a vaginal strip, a vaginal capsule, a bioadhesive film, a sponge or a brush.

The present invention also relates to a use of an iron chelator for inducing senescence in a cancer cell, preferably a hypoxic cancer cell. In a preferred embodiment, the present invention also relates to a use of an iron chelator for inducing apoptosis in a cancer cell, preferably a hypoxic cancer cell.

The present invention also relates to a use of a pharmaceutically compatible iron chelator for the manufacture of a medicament for treating and/or preventing cancer in a subject suspected or known to comprise hypoxic cancer cells.

Further, the present invention relates to a method for inducing an irreversible proliferation arrest in cancer cells comprising
a) contacting said cancer cells with an iron chelator and, thereby,
b) inducing an irreversible proliferation arrest in said cancer cells.

The method of the present invention, preferably, is an in vitro method. The method may, however, also be used in vivo as a method for treating cancer in a subject. Moreover, the method may comprise steps in addition to those explicitly mentioned above. For example, further steps may relate, e.g., to providing cancer cells for step a), or removing the iron chelator after step b). Moreover, one or more of said steps may be performed by automated equipment.

The present invention also relates to a pharmaceutically compatible iron chelator for use in inducing an irreversible proliferation arrest in hypoxic cancer cells.

Furthermore, the present invention relates to a kit comprising an iron chelator and at least one anti-cancer agent.

The term "kit", as used herein, refers to a collection of the aforementioned components. Preferably, said components are combined with additional components, preferably within an outer container. The outer container, also preferably, comprises instructions for carrying out a method of the present invention. Examples for such components of the kit as well as methods for their use have been given in this specification. The kit, preferably, contains the aforementioned components in a ready-to-use formulation. Preferably, the kit may additionally comprise instructions, e.g., a user's manual for applying the iron chelator with respect to the applications provided by the methods of the present invention. Details are to be found elsewhere in this specification. Additionally, such user's manual may provide instructions about correctly using the components of the kit. A user's manual may be provided in paper or electronic form, e.g., stored on CD or CD ROM. The present invention also relates to the use of said kit in any of the methods according to the present invention. Preferably, the anti-cancer agent is an inducer of mTOR activity, a chemotherapeutic agent, an anti-hormone therapeutic agent, a targeted therapy agent, or an immunotherapy agent, as specified herein above.

Further, the present invention relates to a combined preparation comprising a pharmaceutically compatible iron chelator and an anticancer agent for use in treating and/or preventing a cancer forming at least one tumor mass, preferably at least one tumor mass having a diameter of at least 1 mm, preferably at least 5 mm, more preferably at least 10 mm.

The present invention moreover relates to a composition comprising a pharmaceutically compatible iron chelator and a pharmaceutically compatible carrier.

The terms "combined preparation" and "pharmaceutical composition", as used herein, relate to the compounds of the present invention and optionally one or more pharmaceutically acceptable carrier, i.e. excipient. The compounds of the present invention can be formulated as pharmaceutically acceptable salts. Acceptable salts comprise acetate, methyl ester, HCl, sulfate, chloride and the like. The pharmaceutical compositions are, preferably, administered locally, topically or systemically, preferably are administered topically. Suitable routes of administration conventionally used for drug administration are oral, intravenous, or parenteral administration as well as inhalation. A further preferred route of administration is intra-tumoral administration. However, depending on the nature and mode of action of a compound, the pharmaceutical compositions may be administered by other routes as well.

Moreover, the compounds can be administered in combination with other drugs either in a common pharmaceutical composition or as separated pharmaceutical compositions wherein said separated pharmaceutical compositions may be provided in form of a kit of parts. The compounds are, preferably, administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables.

The excipient(s) must be acceptable in the sense of being compatible with the other ingredients of the formulation and being not deleterious to the recipient thereof. The excipient employed may be, for example, a solid, a gel or a liquid carrier. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pa. The diluent(s) is/are selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, non-immunogenic stabilizers and the like.

A therapeutically effective dose refers to an amount of the compounds to be used in a pharmaceutical composition of the present invention which prevents, ameliorates or treats the symptoms accompanying a disease or condition referred to in this specification. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The dosage regimen will be determined by the attending physician and other clinical factors; preferably in accordance with any one of the above described methods. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment. A typical dose can be, for example, in the range of 1 to 1000 µg for a polypeptide or polynucleotide, or 104-108 viral particles for a virus or a virus-like particle; however, doses below or above this exemplary range are envisioned, especially considering the aforementioned factors. Progress can be monitored by periodic assessment. The pharmaceutical compositions and formulations referred to herein are administered at least once in order to treat or ameliorate or prevent a disease or condition recited in this specification. However, the said pharmaceutical compositions may be administered more than one time, for example from one to four times daily up to a non-limited number of days. Specific pharmaceutical compositions are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent, or enclosed or encapsulated in a capsule, sachet, cachet, paper or other suitable containers or vehicles. The resulting formulations are to be adapted to the mode of administration, i.e. in the forms of tablets, capsules, suppositories, solutions, suspensions or the like. Dosage recommendations shall be indicated in the prescribers or users instructions in order to anticipate dose adjustments depending on the considered recipient.

In a preferred embodiment, the present invention also relates to a pharmaceutically compatible iron chelator or a prodrug thereof for use in treating and/or preventing cancer in a subject suspected or known to comprise normoxic cancer cells. Also in a preferred embodiment, the present invention relates to a use of a pharmaceutically compatible iron chelator or prodrug thereof for the manufacture of a medicament for treating and/or preventing cancer in a subject suspected or known to comprise normoxic cancer cells.

Preferably, in said method, said treating and/or preventing comprises induction of senescence in said cancer cells, preferably comprises induction of senescence and apoptosis in said cancer cells, and/or comprises avoiding induction of a Senescence-Associated Secretory Phenotype (SASP) in non-cancer cells.

The terms "normoxic" and "normoxia", preferably, are understood by the skilled person to relate to a an oxygen tension essentially corresponding to the oxygen tension in normal air under standard pressure. Preferably, a normoxic condition (normoxia) is an oxygen tension of at least 40 mmHg, preferably at least 800 mmHg, more preferably at least 120 mmHg. Also preferably, a hypoxic condition (hypoxia) is an oxygen saturation of at least 5%, preferably at least 10%, more preferably at least 15%. Correspondingly, the term "normoxic cancer cell", as used herein, relates to a cancer cell existing or maintained under normoxia as specified above. As will be understood by the skilled person, in a living tissue perfused by blood, i.e. preferably, in situ in a subject, oxygen supply may also be determined by determining oxygen saturation of hemoglobin, e.g. by diffuse optical spectroscopic imaging with near infrared light. Thus, preferably, normoxic cancer cells are cells in a tissue, in particular in a tumor, in which the oxygen saturation of hemoglobin is at least 75%, more preferably at least 85%, most preferably at least 90%. Also preferably, normoxic cancer cells are cells comprised in a tumor mass having a diameter of at most 1 mm, preferably at most 0.5 mm, more preferably at least at most 0.25 mm. Most preferably, normoxic cancer cells are cancer cells not forming a tumor.

Preferably, the term "non-cancer cell" relates to any cell not being a cancer cell. Preferably, the non-cancer cell is a normal cell of a tissue, organ and/or subject. More preferably, the non-cancer cell is a terminally differentiated cell. Also preferably, the non-cancer cell is a "bystander cell", i.e. a non-malignant cell in the vicinity of a tumor. More preferably, the non-cancer cell is a fibroblast.

Advantageously and preferably, it was found in the experiments underlying the present invention that administration of an iron chelator under normoxic conditions induces senescence in cancer cells, which is, upon prolonged incubation, followed by apoptosis. Preferably, it was also found that senescence induction by CPX is mTOR-independent. Pro-senescent anticancer therapies (chemo-, radiotherapy) have to face the obstacle that the concomitant induction of senescence in stromal fibroblasts leads to the secretion of fibroblast proteins (SASP, Senescence-Associated Secretory Phenotype) that can support tumor cell growth and counteract the effects of radio- and chemotherapy. Notably, the protumorigenic and chemoprotective nature of the SASP secreted by stromal fibroblasts is mTOR-dependent (Laberge et al., Nat. Cell Biol. 17: 1049-1061). Since CPX blocks mTOR signaling, CPX acts pro-senescent on tumor cells without inducing the detrimental effects of the SASP secreted from stromal fibroblasts.

In view of the above, the following embodiments are particularly envisaged:

1. A pharmaceutically compatible iron chelator or a prodrug thereof for use in treating and/or preventing cancer in a subject suspected or known to comprise hypoxic cancer cells.

2. The pharmaceutically compatible iron chelator or prodrug thereof for use of embodiment 1, wherein said pharmaceutically compatible iron chelator comprises at least one of a 2-pyridone structure, a hydroxamate structure, a (thio)semicarbazone structure, a bis(2-hydroxyphenyl)-1H-1,2,4-triazol structure, an alpha-hydroxyketone structure, an arylhydrazone structure, and a catechol structure.

3. The pharmaceutically compatible iron chelator or prodrug thereof for use of embodiment 1 or 2, wherein said pharmaceutically compatible iron chelator is a 2-pyridone derivative and/or a prodrug thereof.

4. The pharmaceutically compatible iron chelator or prodrug thereof for use of any one of embodiments 1 to 3, wherein said 2-pyridone derivative and/or prodrug comprises structure

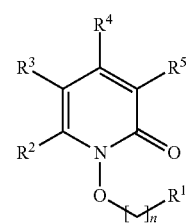

with
n being 0, 1, 2, 3, 4, 5, or 6;
$R^1$ being H, optionally substituted carbonyl, optionally substituted phosphoryl, or optionally substituted sulfonyl;
$R^2$ being selected from cyclohexyl, —H, C1-C6 alkyl, C5-C8 cycloalkyl, C1-C6 alkoxy, and halogen;
$R^4$ being selected from methyl, —H, C1-C6 alkyl, C5-C8 cycloalkyl, C1-C6 alkoxy, and halogen; and
$R^3$ and $R^5$ being independently selected from —H, C1-C6 alkyl, C5-C8 cycloalkyl, C1-C6 alkoxy, and halogen.

5. The pharmaceutically compatible iron chelator for use of any one of embodiments 1 to 4, wherein n=0,
$R^1$ is H, optionally substituted carbonyl, or optionally substituted phosphoryl;
$R^2$ is cyclohexyl;
$R^4$ is methyl; and
$R^3$ and $R^5$ are —H.

6. The pharmaceutically compatible iron chelator for use of any one of embodiments 1 to 5, wherein said pharmaceutically compatible iron chelator is ciclopirox (2(1H)-Pyridinone, 6-cyclohexyl-1-hydroxy-4-methylpyridin-2 (1H)-one; CAS-No: 29342-05-0), preferably ciclopirox olamine.

7. The pharmaceutically compatible iron chelator for use of embodiment 1 or 2, wherein said pharmaceutically compatible iron chelator is (i) a hydroxamate iron chelator, more preferably Deferoxamine (DFO, CAS No. 70-51-9) or hydroxycarbamide (CAS No. 127-07-1, (ii) a (thio)semicarbazone iron chelator, preferably nitrofural (CAS No. 59-87-0), 3-aminopyridine-2-carboxaldehyde Thiosemicarbazone (Triapine, CAS No. 236392-56-6) or 5-Hydroxypyridine-2-carboxaldehyde Thiosemicarbazone (HPCT, CAS No. 19494-89-4), (iii) a bis(2-hydroxyphenyl)-1H-1,2,4-triazol iron chelator, preferably Deferasirox (CAS No. 201530-41-8), iv) an alpha-hydroxyketone iron chelator, preferably Deferiprone (Cas No. 30652-11-0), or (v) N,N'N"-tris(2-pyridylmethyl)-cis,cis-1,3,5-triaminocyclohexane (Tachpyr).

8. The pharmaceutically compatible iron chelator or prodrug thereof for use of any one of embodiments 1 to 7, wherein said hypoxic cancer cells are slowly proliferating or non-dividing hypoxic cancer cells.

9. The pharmaceutically compatible iron chelator or prodrug thereof for use of any one of embodiments 1 to 8, wherein said hypoxic cancer cells are papillomavirus-positive hypoxic cancer cells, preferably are human papillomavirus-positive hypoxic cancer cells.

10. The pharmaceutically compatible iron chelator or prodrug thereof for use of any one of embodiments 1 to 9, wherein hypoxic cancer cells are cells under an oxygen tension of at most 40 mmHg, preferably at most 20 mmHg, more preferably at most 7.5 mmHg.

11. The pharmaceutically compatible iron chelator or prodrug thereof for use of any one of embodiments 1 to 10, wherein hypoxic cancer cells are cells under an oxygen saturation of at most 5%, preferably at most 3%, more preferably at most 1%.

12. The pharmaceutically compatible iron chelator or prodrug thereof for use of any one of embodiments 1 to 11, wherein said cancer forms at least one tumor mass, preferably at least one tumor mass having a diameter of at least 1 mm, preferably at least 5 mm, more preferably at least 10 mm.

13. The pharmaceutically compatible iron chelator or prodrug thereof for use of any one of embodiments 1 to 12, wherein said treating comprises administration of at least one further anticancer therapy.

14. The pharmaceutically compatible iron chelator for or prodrug thereof use of any one of embodiments 1 to 13, wherein said anticancer therapy is radiotherapy, chemotherapy, anti-hormone therapy, targeted therapy, immunotherapy, or any combination thereof.

15. The pharmaceutically compatible iron chelator or prodrug thereof for use of any one of embodiments 1 to 14, wherein said anticancer therapy comprises activation of mTOR signalling.

16. The pharmaceutically compatible iron chelator or prodrug thereof for use of any one of embodiments 1 to 15, wherein said anticancer therapy is administered before or simultaneously with said pharmaceutically compatible iron chelator.

17. The pharmaceutically compatible iron chelator or prodrug thereof for use of any one of embodiments 1 to 16, wherein said treating and/or preventing cancer further comprises abstaining from iron repletion measures, preferably further comprises iron depletion therapy.

18. The pharmaceutically compatible iron chelator or prodrug thereof for use of any one of embodiments 1 to 17, wherein said iron repletion measures comprise at least one of transfusion of blood or a blood product and administration of iron-providing compounds.

19. A pharmaceutically compatible iron chelator or prodrug thereof for use in treatment and/or prevention of a human papillomavirus (HPV) related lesion.

20. The pharmaceutically compatible iron chelator or prodrug thereof for use of embodiment 19, wherein said treatment and/or prevention comprises inducing an irreversible proliferation arrest of HPV-positive cells, preferably of HPV-positive cancer cells.

21. The pharmaceutically compatible iron chelator or prodrug thereof for use of embodiment 19 or 20, wherein said HPV-positive cells are slowly proliferating or non-dividing HPV-positive cells, preferably are hypoxic slowly proliferating or non-dividing HPV-positive cells.

22. The pharmaceutically compatible iron chelator for or prodrug thereof use of any one of embodiments 19 to 21, wherein said treatment and/or prevention further comprises activation of mTOR signalling.

23. The pharmaceutically compatible iron chelator or prodrug thereof for use of any one of embodiments 19 to 22, wherein said treatment and/or prevention comprises topical application of said pharmaceutically compatible iron chelator, preferably to a mucosa and/or a skin.

24. The pharmaceutically compatible iron chelator or prodrug thereof for use of any one of embodiments 19 to 23, wherein said treatment further comprises topical application of said pharmaceutically compatible iron chelator to a hypoxic zone of a tumor.

25. The pharmaceutically compatible iron chelator or prodrug thereof for use of any one of embodiments 19 to 24, wherein said HPV related lesion forms at least one tumor mass, preferably having a diameter of at least 1 mm, preferably at least 5 mm, more preferably at least 10 mm.

26. The pharmaceutically compatible iron chelator or prodrug thereof for use of any one of embodiments 19 to 25, wherein the HPV related lesion is selected from the group consisting of warts, exophytic growing papillomas, condylomata, inverted papillomas, pre-neoplastic HPV-induced lesions, and neoplastic HPV-induced lesions.

27. The pharmaceutically compatible iron chelator or prodrug thereof for use of any one of embodiments 19 to 26, wherein said HPV-related lesion is a neoplastic HPV-related lesion selected from the list consisting of cervical neoplasia, rectal neoplasia, neoplasia of the anal epithelium, neoplasia of the oropharynx, and neoplasia of the tonsils.

28. The pharmaceutically compatible iron chelator or prodrug thereof for use of any one of embodiments 19 to 27, wherein said pharmaceutically compatible iron chelator is provided on a polymer carrier comprising at least one of cotton, cellulose, dextran, polyethylene, polypropylene, poly(dimethylsiloxane), ethylene vinyl acetate copolymers, polycarophil, hydroxypropyl methylcellulose and polyacrylic acids.

29. The pharmaceutically compatible iron chelator or prodrug thereof for use of embodiment 28, wherein the polymer carrier is a cervical cap, a swab, a tampon, a vaginal ring, a vaginal strip, a vaginal capsule, a bioadhesive film, a sponge or a brush.

30. The pharmaceutically compatible iron chelator or prodrug thereof for use of any one of embodiments 19 to 29, wherein said pharmaceutically compatible iron chelator is a 2-pyridone derivative, preferably a 2-pyridone derivative having a structure as specified in any one of embodiments 2 to 7.

31. The pharmaceutically compatible iron chelator or prodrug thereof for use of any one of embodiments 19 to 30, wherein said pharmaceutically compatible iron chelator is provided as a prodrug.

32. Use of an iron chelator or prodrug thereof for inducing senescence or, preferably, apoptosis, in a cancer cell, preferably a hypoxic cancer cell.

33. Use of a pharmaceutically compatible iron chelator or prodrug thereof for the manufacture of a medicament for treating and/or preventing cancer in a subject suspected or known to comprise hypoxic cancer cells.

34. A method for inducing an irreversible proliferation arrest in cancer cells comprising
a) contacting said cancer cells with an iron chelator or prodrug thereof and, thereby,
b) inducing an irreversible proliferation arrest in said cancer cells.

The method of embodiment 34, wherein said cancer cells are hypoxic cancer cells and/or wherein said cancer cells are maintained under hypoxic conditions.

36. A pharmaceutically compatible iron chelator or prodrug thereof for use in inducing an irreversible proliferation arrest in hypoxic cancer cells.

37. The pharmaceutically compatible iron chelator or prodrug thereof for use of embodiment 36, wherein said irreversible proliferation arrest is senescence, or, preferably, apoptosis.

38. A kit comprising an iron chelator or prodrug thereof and at least one anti-cancer agent.

39. The kit of embodiment 38, wherein said anti-cancer agent is an inducer of mTOR activity, a chemotherapeutic agent, an anti-hormone therapeutic agent, a targeted therapy agent, or an immunotherapy agent.

40. A pharmaceutical composition comprising a pharmaceutically compatible iron chelator or prodrug thereof and a pharmaceutically compatible carrier for use in treating and/or preventing cancer in a subject suspected or known to comprise hypoxic cancer cells.

41 A combined preparation comprising a pharmaceutically compatible iron chelator or prodrug thereof and an anticancer agent for use in treating and/or preventing a cancer forming at least one tumor mass, preferably at least one tumor mass having a diameter of at least 1 mm, preferably at least 5 mm, more preferably at least 10 mm.

42. The pharmaceutically compatible iron chelator or prodrug thereof for use according to any one of embodiments 1 to 18, the method according to embodiment 34 or 35, or the combined preparation for use of embodiment 41, wherein said cancer is at least T1, preferably T2 according to the World Health Organization (WHO) TNM classification.

43. A pharmaceutically compatible iron chelator or a prodrug thereof for use in treating and/or preventing cancer in a subject suspected or known to comprise normoxic cancer cells.

44. The pharmaceutically compatible iron chelator or a prodrug thereof for use of embodiment 43, wherein said treating and/or preventing comprises induction of senescence in said cancer cells.

45. The pharmaceutically compatible iron chelator or a prodrug thereof for use of embodiment 43 or 44, wherein said treating and/or preventing comprises induction of senescence and apoptosis in said cancer cells.

46. The pharmaceutically compatible iron chelator or a prodrug thereof for use of any one of embodiments 43 to 45, wherein said treating and/or preventing comprises avoiding induction of a Senescence-Associated Secretory Phenotype (SASP) in non-cancer cells, preferably in stromal fibroblasts.

47. The pharmaceutically compatible iron chelator or a prodrug thereof for use of any one of embodiments 43 to 46, wherein said iron chelator or a prodrug thereof is a compound as specified in any one of embodiments 2 to 7.

48. Use of a pharmaceutically compatible iron chelator or prodrug thereof for the manufacture of a medicament for treating and/or preventing cancer in a subject suspected or known to comprise normoxic cancer cells.

All references cited in this specification are herewith incorporated by reference with respect to their entire disclosure content and the disclosure content specifically mentioned in this specification.

FIGURE LEGENDS

FIG. 1: Senescence assays (A) and colony formation assays (B) of HeLa cells after treatment with 10 µM CPX or solvent control EtOH.

Figure 2:
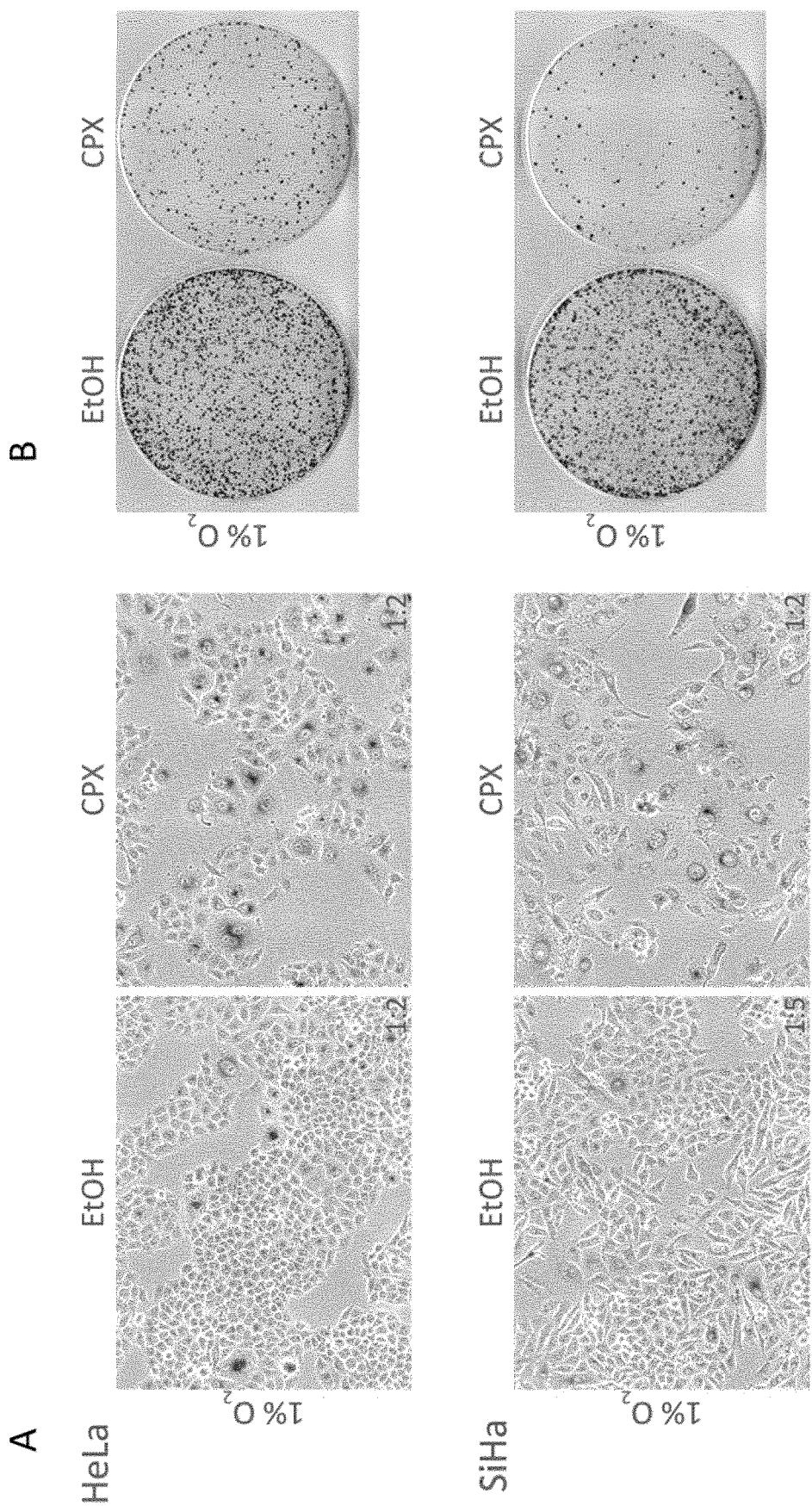

FIG. 2: Senescence assays (A) and colony formation assays (B) of HPV18-positive HeLa and HPV16-positive SiHa cells under hypoxic conditions (1% $O_2$).

Figure 3:
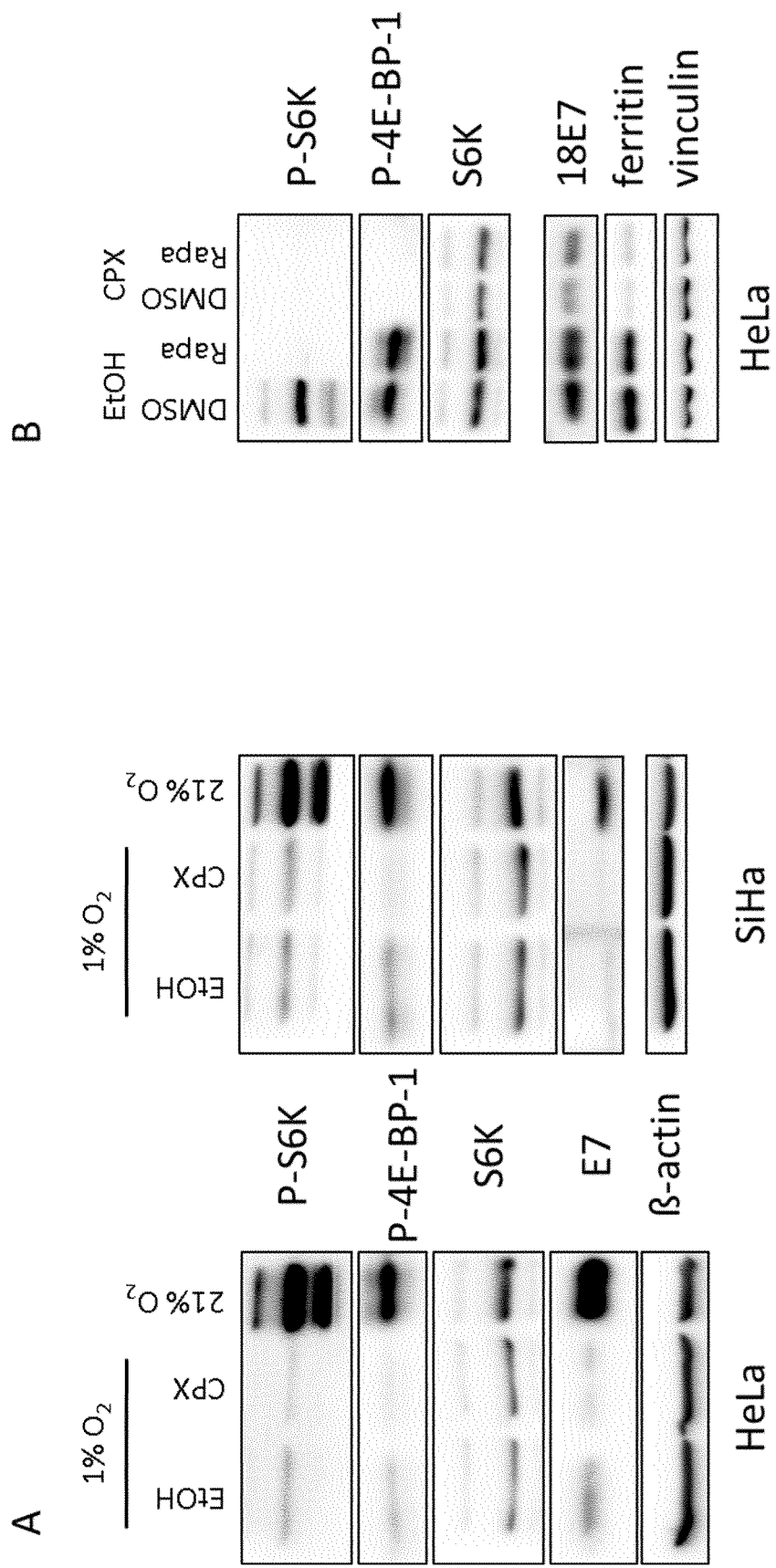

FIG. 3: Western blots of the indicated proteins in extracts from cells of Example 3.

Figure 4:
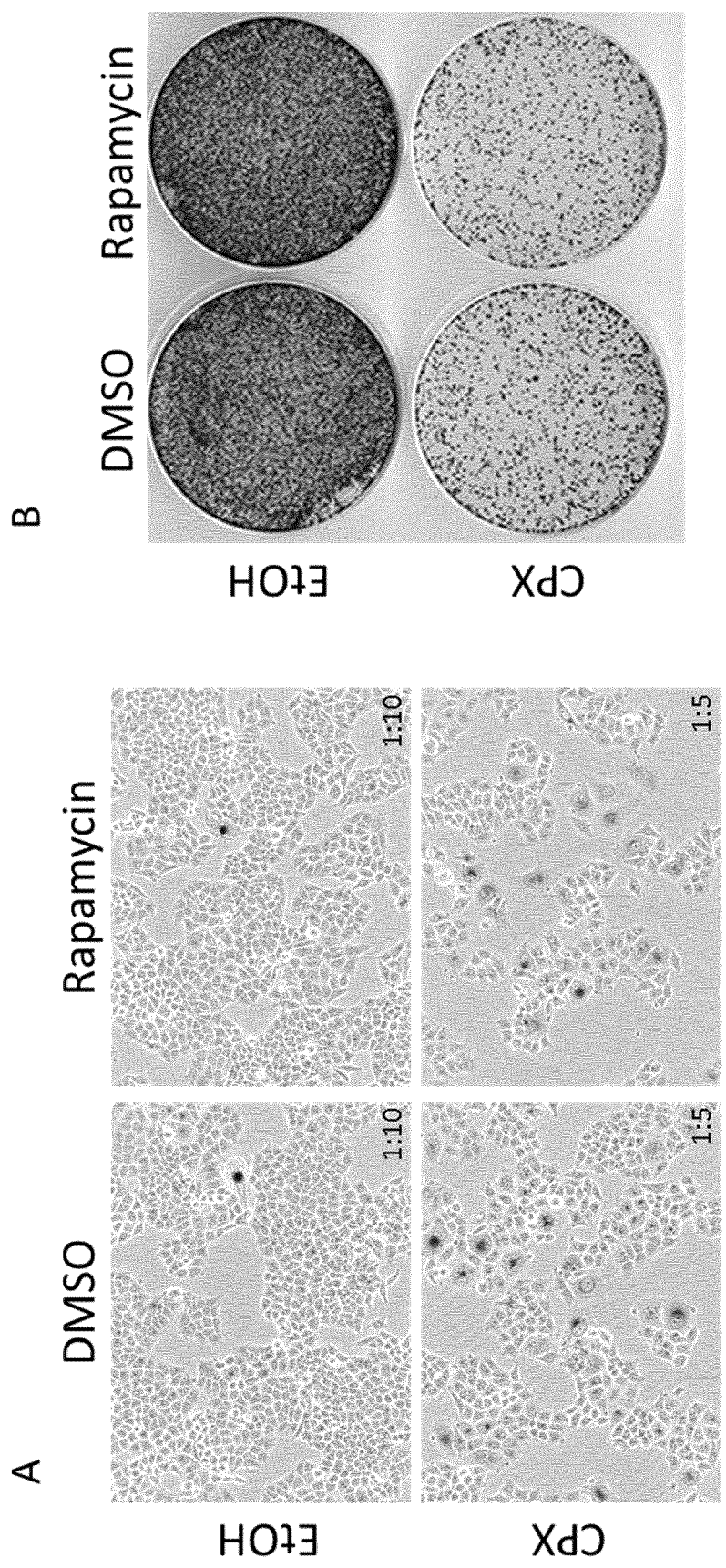

FIG. 4: Senescence assays (A) and colony formation assays (B) in the presence of CPX and/or rapamycin.

Figure 5:
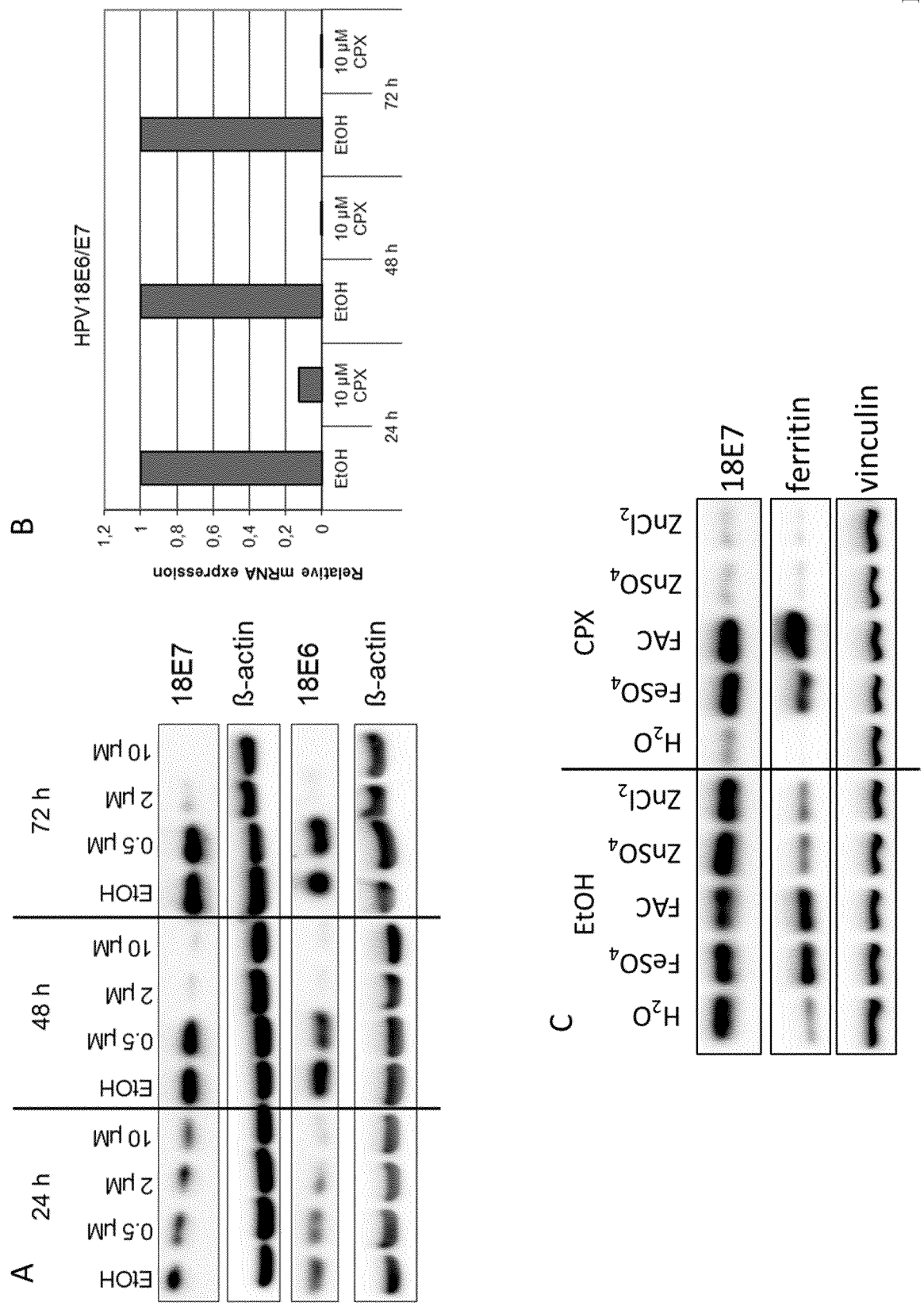

FIG. 5: Effect of CPX on HPV E6 and E7 expression: (A) E6 and E7 western blots on protein extracts of cells of Example 6; (B) relative E6/E7 mRNA quantification; (C) effect of iron or zink substitution of E7 and ferritin expression (western blot).

Figure 6:
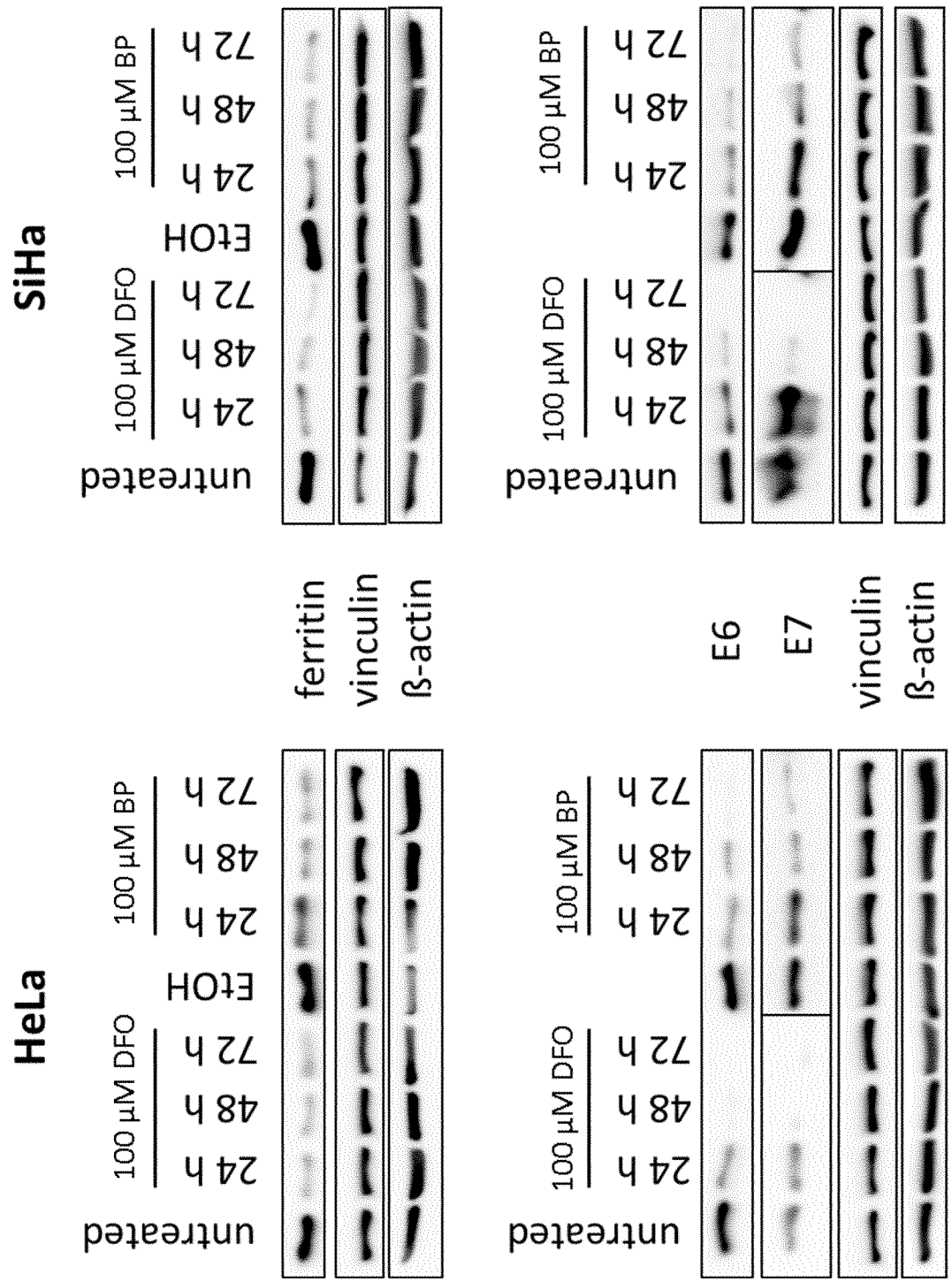

FIG. 6: Other iron chelators also repress HPV E6 and E7: DFO and BP also reduce both HPV18 and HPV16 E6 and E7 protein levels, indicating that the repression is linked to the deprivation of intracellular iron levels.

Figure 7:
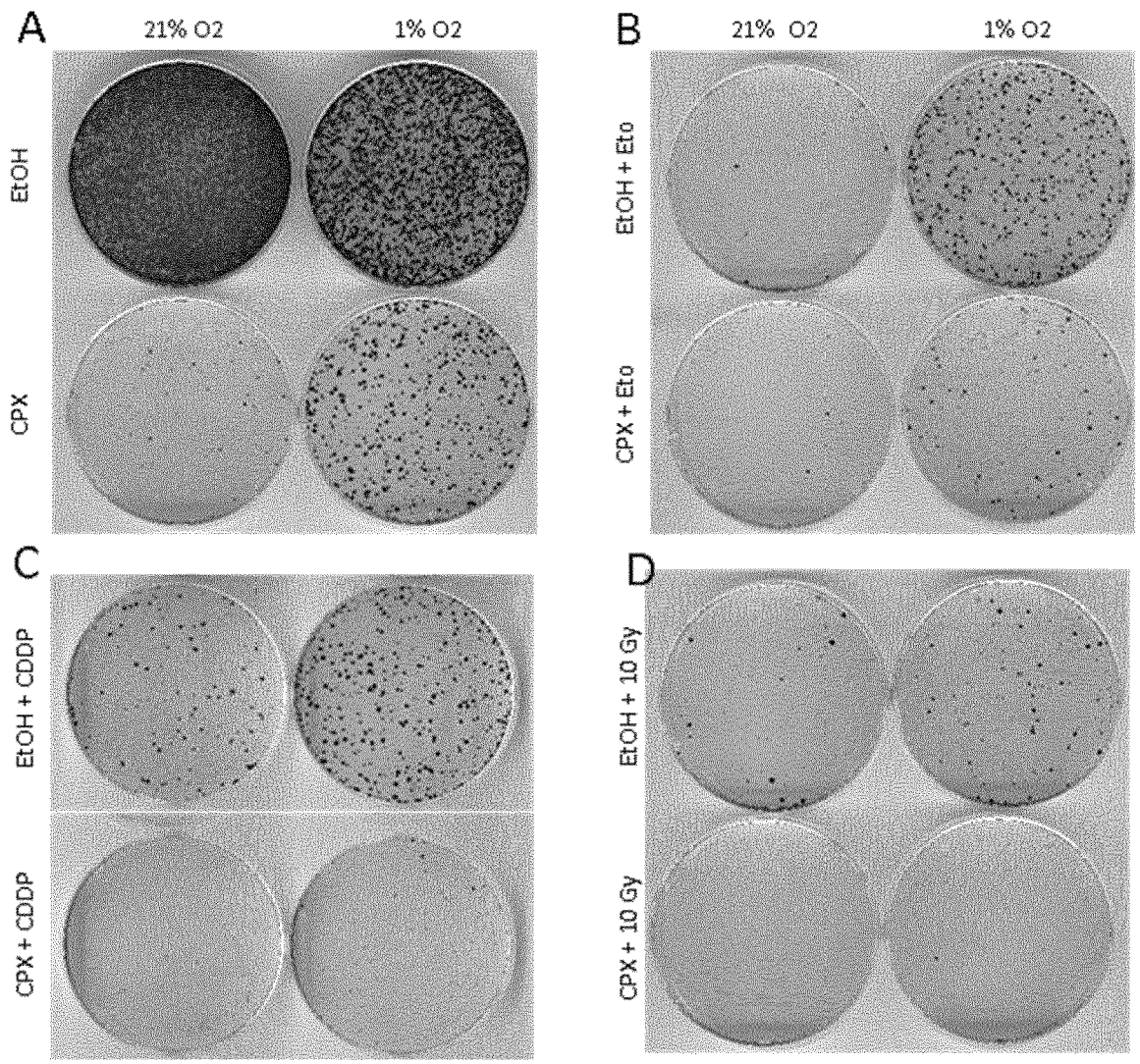

FIG. 7: Colony formation assays of HeLa cells after treatment with CPX and etoposide, cisplatin or irradiation under normoxia or hypoxia: Colony formation assay of HeLa cells after treatment with CPX under normoxia and hypoxia for 4d (A), treatment with CPX in combination with 5 µM etoposide (B), 5 µM CDDP (cisplatin, C) or irradiation with 10 Gy (D) under normoxia and hypoxia.

Figure 8:
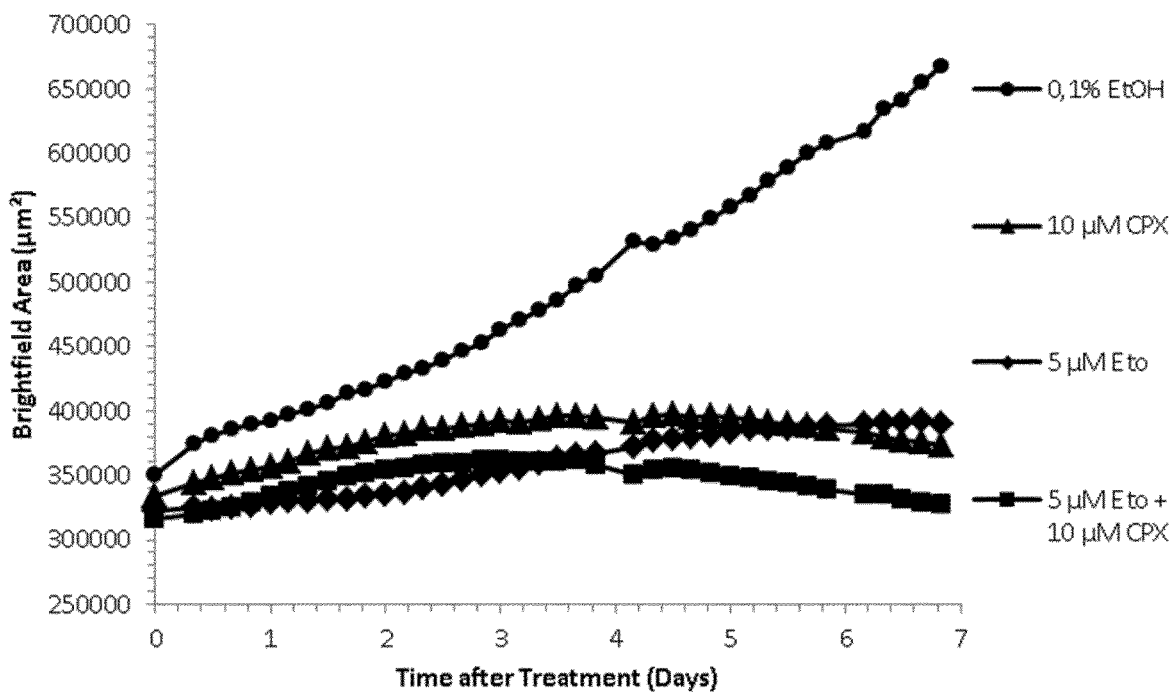
Figure 8:
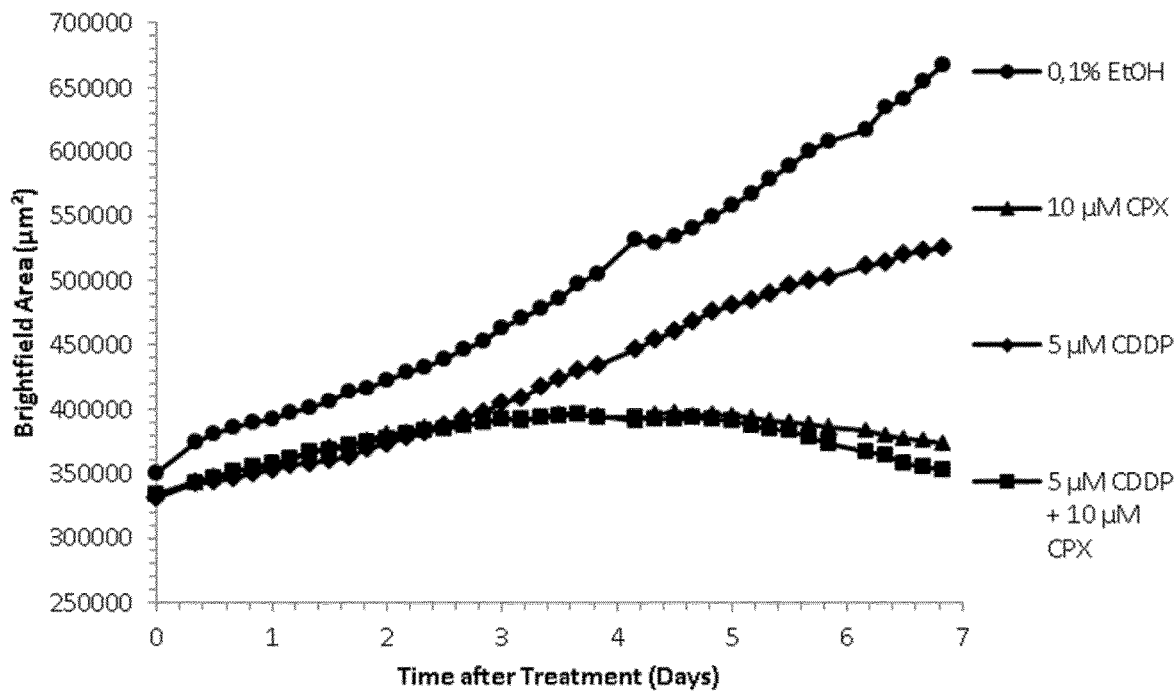

FIG. 8: Combinatorial treatments of 3-dimensional cell aggregates (spheroids) with CPX in combination with etoposide or cisplatin under normoxic conditions. (A) HeLa spheroid growth after treatment with 10 µM CPX, 5 µM etoposide or a combination of both. (B) HeLa spheroid growth after treatment with 10 µM CPX, 5 µM CDDP (cisplatin) or a combination of both.

Figure 9:
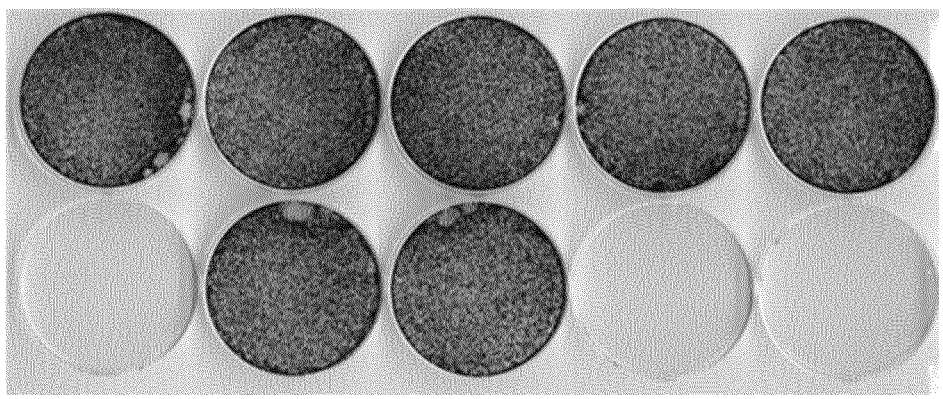
Figure 9:
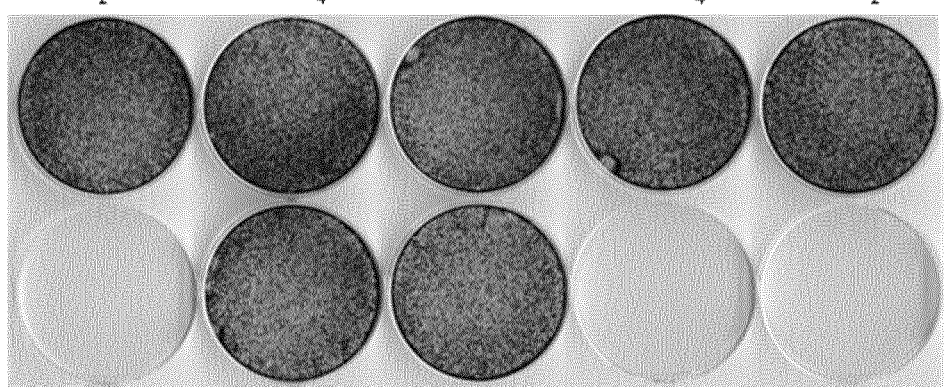
Figure 9:
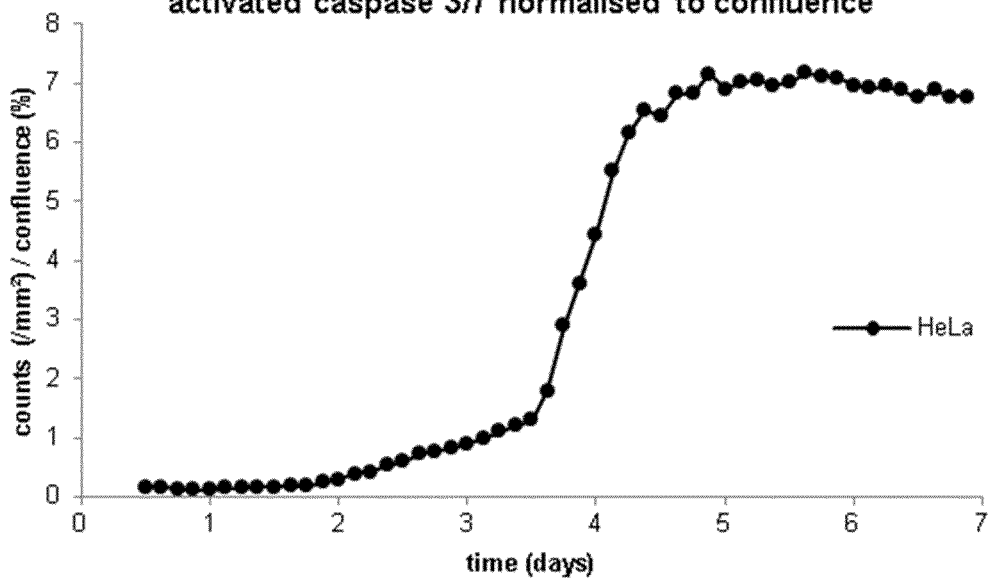
Figure 9:
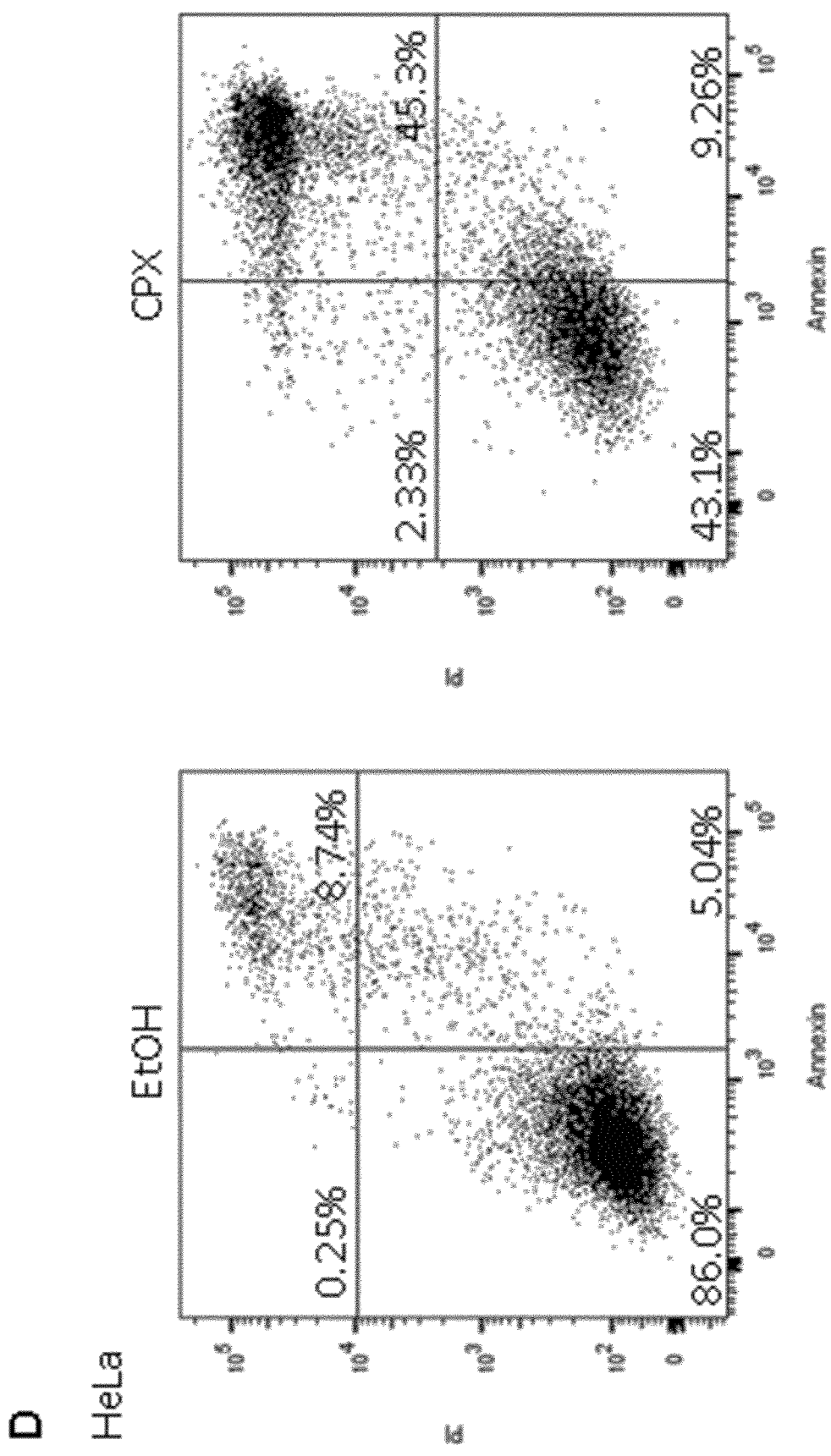

FIG. 9: CPX also induces apoptosis under normoxic conditions. Depending on treatment duration, senescence or apoptosis is induced. 48 h treatment leads to the induction of senescence. 5 d treatment (A and B) induces apoptosis and hence no colonies grow out after release in colony formation assays. C: activation of caspase 3/7 (apoptosis marker) upon CPX treatment; D: 72 h treatment with CPX, cells were stained with the Annexin V and PI: Annexin V positive, PI negative cells represent early apoptotic cells; Annexin V positive, PI positive cells represent late apoptotic cells.

Figure 10:
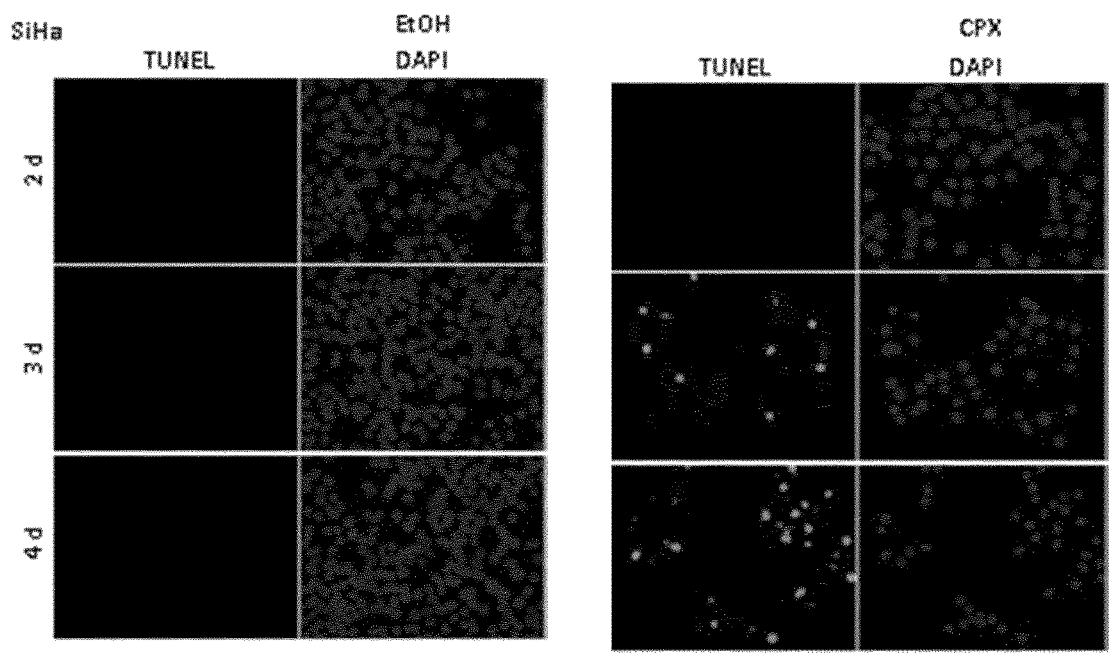
Figure 10:
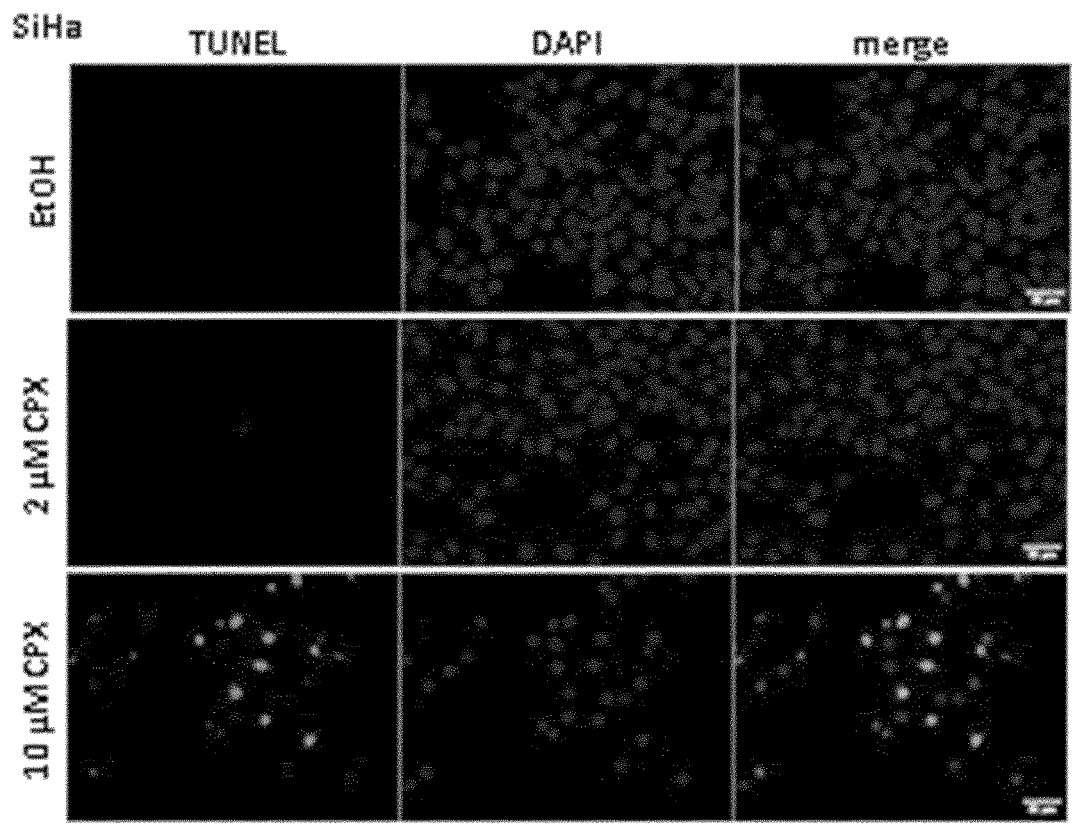

FIG. 10: TUNEL assay (bright cells=apoptotic cells) under normoxic conditions with the indicated cell lines; A: time kinetic of 10 µM CPX; B: dose kinetic of 96 h CPX treatment.

Figure 11:
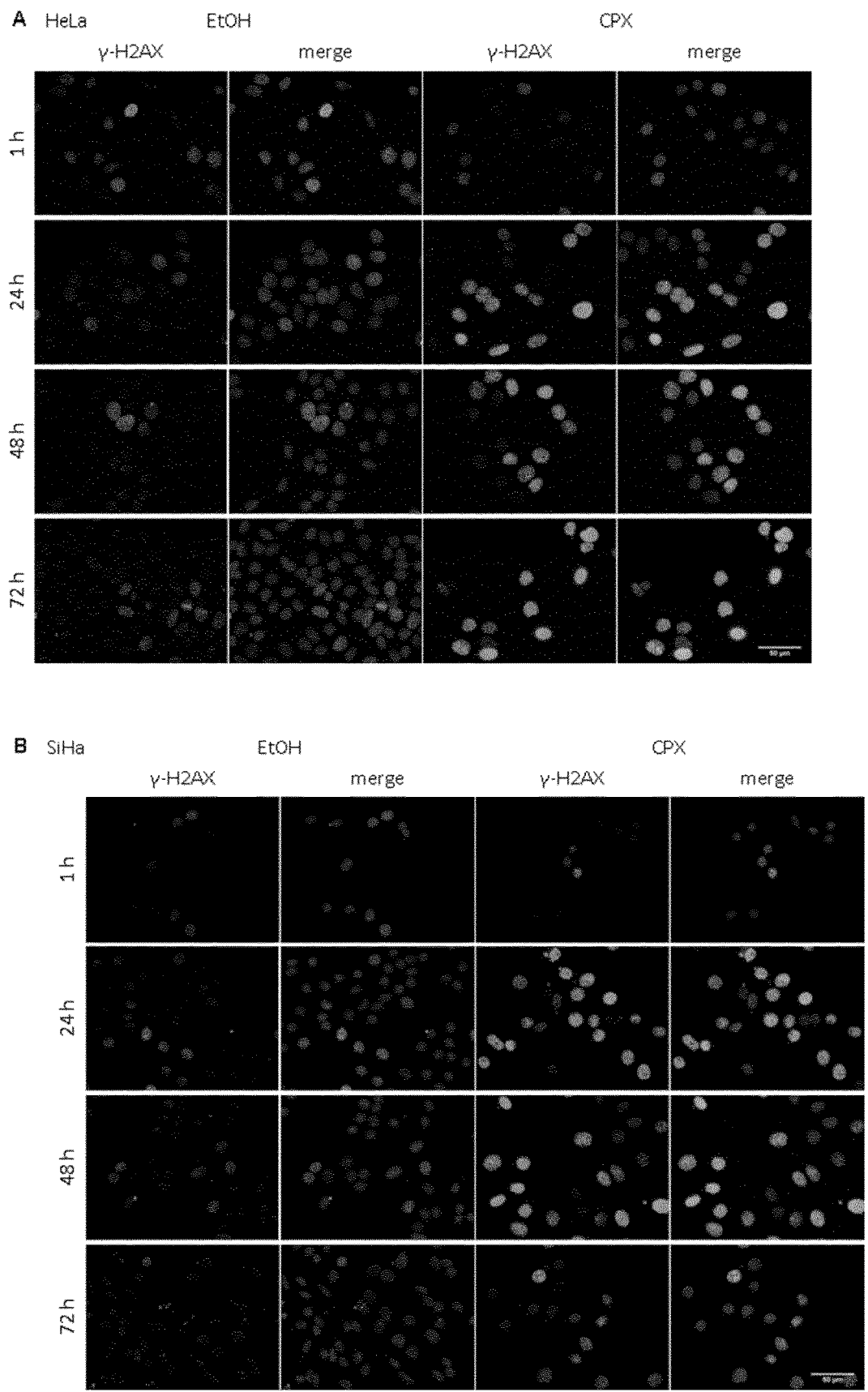

FIG. 11: CPX induces DNA damage (gamma-H2AX=DNA damage marker) under normoxic conditions.

Figure 12:
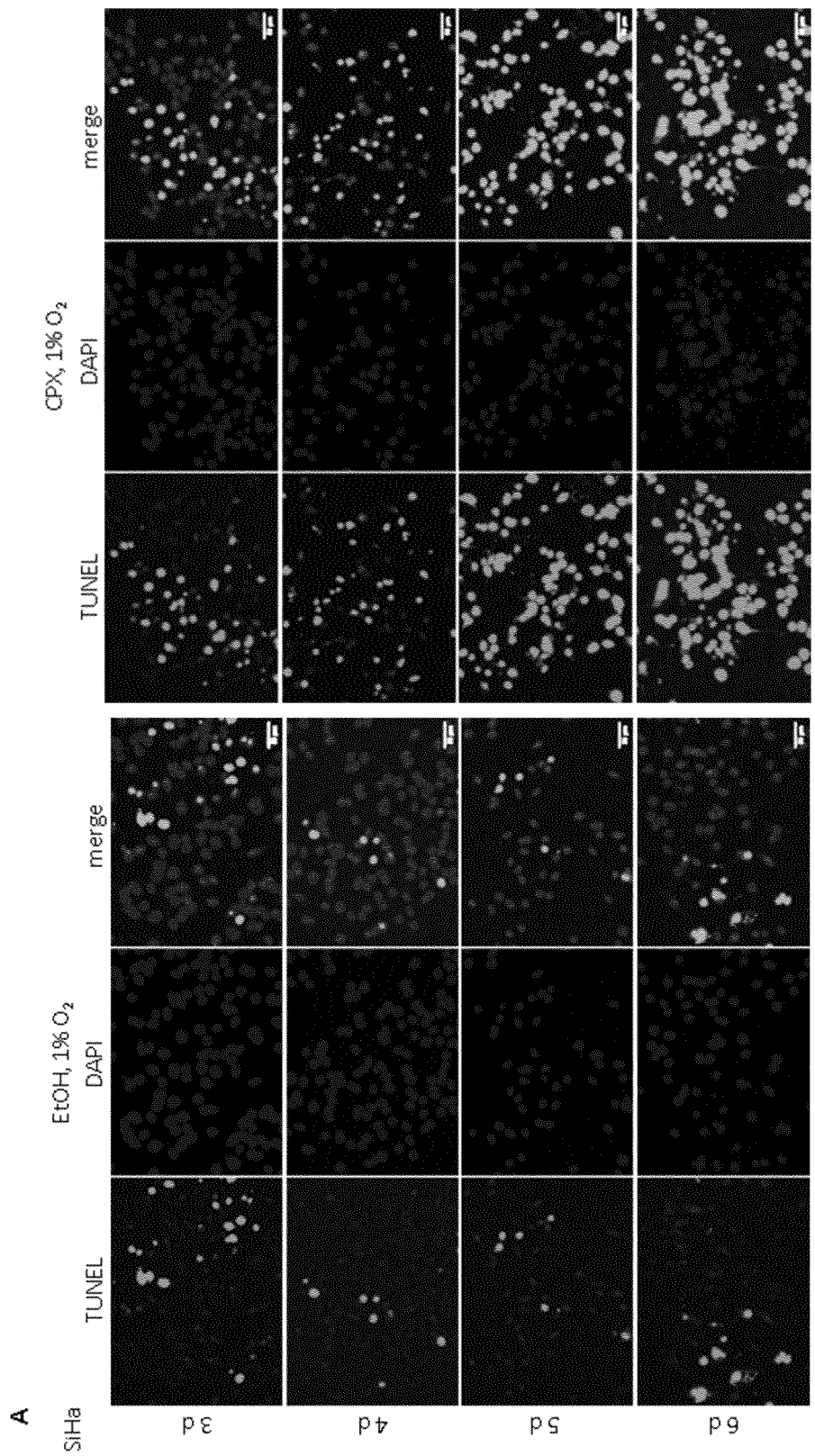
Figure 12:
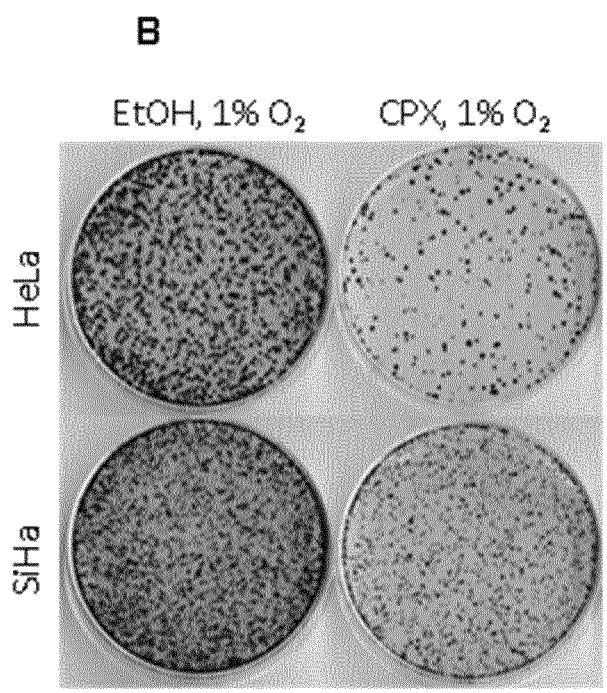

FIG. 12: CPX can induce apoptosis under hypoxic conditions. A) TUNEL assay (green cells=apoptotic cells), EtOH=solvent control. B) Colony Formation Assay upon CPX treatment of hypoxic HeLa and SiHa cells.

The following Examples shall merely illustrate the invention. They shall not be construed, whatsoever, to limit the scope of the invention.

EXAMPLE 1: METHODS

Cell Culture

HPV18-positive HeLa cells were bought from American Type Culture Collection (ATCC).

Cells were cultured in Dulbecco's Modified Eagle's Medium (DMEM) supplemented with 10% fetal bovine serum (FBS), 5% penicillin (100 U/ml), streptomycin (100 µg/ml) and 2 mM L-glutamine under normoxic (37° C., 21% $O_2$, 5% $CO_2$) conditions.

Iron Chelators

For all experiments CPX olamine compound from Sigma-Aldrich (C0415-1G) was utilized, stored at room temperature. The powder was diluted in 100% EtOH and prepared freshly for every experiment. Therefore, EtOH was used as a solvent control in experiments performed with CPX. Stock solutions of 10 mM were prepared and diluted 1:1000 in medium for the treatment of cells. DFO from Sigma-Aldrich was used as a deferoxamine mesylate salt. DFO was stored as a powder at −20° C. and diluted in distilled $H_2O$ to a stock solution of 100 mM, which can be stored at −20° C. for 7 days. For the treatment of cells DFO stock was diluted 1:1000 in medium. BP from Sigma-Aldrich was dissolved in ethanol (100 mM, stable for several months) and used for the treatment of cells with a final concentration of 100 µM.

Cell Treatment

Cells were seeded in 6 cm (21 cm2) Greiner cell culture dishes containing 3 ml DMEM medium to reach 20-30% confluency after 24 h. Then the medium was exchanged for medium containing iron chelators. In some experiments CPX was pre-incubated with either iron- or zinc-containing agents. EtOH and 10 µM CPX were either pre-incubated with $H_2O$, 6.67 µM ferric ammonium citrate (FAC), iron sulfate (FeSO4), zinc chloride (ZnCl2) or zinc sulfate (ZnSO4) for 10 min prior to cell treatment.

Cell Counting

For cell counting experiments and cell growth analysis cell numbers were determined in duplicates by trypan blue technique using Countess™ Automated Cell Counter. Furthermore the IncyCyte S3 system was used to determine cell proliferation.

Colony Formation Assay (CFA)

The ability to form colonies of a treated cell comparable to an untreated cell after iron chelation was tested performing a colony formation assay (CFA). In order to do this, cells were fixed and cell nuclei stained with crystal violet (hexamethyl pararosaniline chloride). After treatment cells were splitted 1:100 and 1:200 into new dishes and cultured for another 5-10 days at 37° C. in normal DMEM to display the amount of still growing cells after treatment. Subsequently, cells were fixed and stained with 350 µl formaldehyde-crystal violet for 3 min and washed with $H_2O$. For quantification with the photometer, cells were discoloured with 33% acidic acid. Images were made with Epson Perfection 4990 Photo Scanner.

Senescence Assay

Treated cells were stained for senescence-associated beta-galactosidase (SA-beta-gal) activity at pH 6. Dimri et. al. could show that the marker SA-beta-gal is only expressed in senescent fibroblasts and keratinocytes, excluding pre-senescent, quiescent and differentiated cells (Dimri et al. 1995). The activity of SA-beta-gal can be determined by adding 5-Brom-4-chlor-3-indoxyl-beta-D-galactopyranosid (X-gal), which is then hydrolyzed by the galactosidase enzyme into galactose and 5-bromo-4-chloro-3-hydroxyindole. Dimerization of the latter followed by oxidation results in the formation of an insoluble blue product 5,5'-dibromo-4,4'-dichloro-indigo, which can be detected by a brightfield microscope. After treatment with iron chelators, the cells were splitted usually 1:2, 1:5 and 1:10 and cultured for 3-4 days in normal DMEM. Then the cells were washed, fixed with 1% formaldehyde/0.2% glutaraldehyde in PBS for 3 min followed by another wash with PBS. Fixed cells were incubated with 1.5 ml in senescence assay buffer mix overnight at 37° C. Then cells were washed again with PBS and SA-beta-gal positivity was detected under a brightfield microscope. Cells that are positive for SA-β-gal activity are blue.

EXAMPLE 2: SENESCENCE AND COLONY FORMATION CAPACITY OF HELA CELLS AFTER TREATMENT CPX

In general, E6/E7 repression leads to the induction of senescence. Under hypoxia, however, the impaired mTOR pathway prevents efficient senescence induction and cells escape from anti-proliferative treatments like chemotherapy or radiotherapy. Ciclopirox (CPX) or EtOH were incubated with either $H_2O$, 6.67 µM $FeSO_4$, FAC, $ZnSO_4$ or $ZnCl_2$ for 10 min prior to addition on HeLa cells. CPX induces senescence, indicated by the dark cells in the senescence assays (FIG. 1A) and induction of senescence by CPX reduces colony forming capacity (FIG. 1B). The effect of CPX can be rescued by the addition of iron ($FeSO_4$ or FAC), but not zinc ($ZnSO_4$ or $ZnCl_2$), indicating that the effects are a result of iron depletion. Thus, the iron chelator CPX induces senescence under normoxia which can be reverted by the addition of iron (but not zinc), indicating that it is caused by the loss of iron.

EXAMPLE 3: SENESCENCE AND COLONY FORMATION CAPACITY OF HPV18-POSITIVE HELA AND HPV16-POSITIVE SIHA CELLS UNDER HYPOXIC CONDITIONS

Cells were cultured for 24 h under hypoxic conditions (1% 02) and then treated with 10 µM CPX or solvent control EtOH for another 72 h under hypoxic conditions. CPX treated cells still undergo senescence even under hypoxia (FIG. 2A) and the colony forming capacity is impaired (FIG. 2B). Thus, interestingly (and despite E6/E7 inhibition under hypoxia) CPX can induce senescence and reduce colony forming capacity even under hypoxic conditions

EXAMPLE 4: EFFECT OF CPX ON MTOR SIGNALING

In the same experimental setup as in Example 3, proteins were extracted at the end of CPX treatment. Under hypoxic conditions mTOR signaling is impaired as indicated by the lack of phosphorylated substrates of the active mTOR pathway (FIG. 3A, P-S6K and P-4E-BP-1). CPX treatment under hypoxia does not reconstitute mTOR signaling in HeLa and SiHa cells. Notably, CPX acts as an mTOR inhibitor, since under normoxic conditions protein levels of P-S6K and P-4E-BP-1 are decreased (similar to treatment with the mTOR inhibitor rapamycin, FIG. 3B). Thus, CPX does not reconstitute mTOR signaling, but rather acts as an mTOR inhibitor.

EXAMPLE 5: CPX INDUCES SENESCENCE INDEPENDENT OF ACTIVE MTOR SIGNALING

HeLa cells were treated simultaneously with 10 µM CPX and 50 nM rapamycin (a chemical mTOR inhibitor) for 48 h. Even in the presence of rapamycin, CPX still induces senescence (FIG. 4A) and reduces the colony forming capacity (FIG. 4B), Thus, CPX-induced senescence is mTOR independent. Proteins that show the downregulation of phosphorylated substrates of the active mTOR signaling upon rapamycin treatment are displayed in FIG. 3B.

EXAMPLE 6: EFFECT OF CPX ON HPV E6/E7 EXPRESSION

HPV18-positive HeLa cells were treated with different concentrations of CPX for 24, 48 and 72 h. Immunoblot analyses show that CPX decreases E6 and E7 protein levels in a time- and dose-dependent manner (FIG. 5A). E6/E7 are also downregulated at the mRNA level (FIG. 5B, qPCR analyses). Furthermore the repression of E6/E7 is linked to the depletion of iron, since the pre-incubation of 10 µM CPX with 6.67 µM iron (FeSO4 and FAC) but not zinc (ZnSO4 and ZnCl2) can prevent the repression of E7 (FIG. 5C). CPX reduces HPV E6/E7 on protein and mRNA level in an iron-dependent manner. Accordingly, like senescence induction, oncogene repression by CPX is linked to iron deprivation, since saturation of CPX with iron (but not zinc) inhibits the repression.

EXAMPLE 7: OTHER IRON CHELATORS

Other clinical iron chelators, Deferoxamin (DFO) and Bipyridil (BP) also repress HPV E6 and E7: DFO and BP also reduce both HPV18 and HPV16 E6 and E7 protein levels, indicating that the repression is linked to the deprivation of intracellular iron levels (FIG. 6)

EXAMPLE 8: DOUBLE TREATMENT WITH CPX AND CANCER THERAPEUTICS

HeLa cells were treated with 10 µM CPX or EtOH (FIG. 7A) or in combination with the chemotherapeutic drug etoposide (5 µM) for 72 h at 210% or 1% O2 (FIG. 7B). After treatment colonies were stained with crystal violet. The results of treatment with cisplatin or irradiation with 10 Gy instead of etoposide treatment are shown in FIGS. 7C and D. The colony formation assays after combinatorial treatments of CPX with either etoposide, cisplation or irradiation therapy show that CPX can target the cells that escape from chemotherapy/radiotherapy under hypoxia, but also under normoxia.

EXAMPLE 9: EFFECT OF CPX ON 3D CELL SPHEROIDS

Generation and treatment of spheroids: 5000 cells (HeLa) were seeded in 200 µl DMEM+30% methylcellulose stock solution in a low attachment U-bottom 96-well plate. After 3 days, half of the medium was removed and replaced with media containing drugs or solvent control. After 3 days half of the medium was replaced with fresh medium plus drugs. Spheroid size was monitored using the IncuCyte S3 live imaging system. As shown in FIG. 8, there is a clear inhibition of 3D spheroid growth by CPX. There is also a cooperative effect of CPX+chemotherapy in inhibiting the growth of 3D cell spheroids already under normoxic conditions.

EXAMPLE 10: EFFECT OF CPX UNDER NORMOXIC CONDITIONS

While inducing senescence in cancer cells under normoxia and after short-term incubation (Example 2), CPX was found to induce apoptosis after longer-term incubation, e.g. after 3 to 4 days (FIGS. 9 and 10). Moreover, it was surprisingly found tat CPX can also induce DNA damage in cancer cells (FIG. 11).

EXAMPLE 11: INDUCTION OF APOPTOSIS BY CPX UNDER ANAEROBIC CONDITIONS

As shown in FIG. 12, CPX can also induce apoptosis after 3 to 4 days of anaerobic incubation in cancer cells.

The following non-standard literature was cited:
1. de Martel et al. Int J Cancer, 2017. 141(4): p. 664-670.
2. Dyson et al., Science, 1989, 243(4893): p. 934-7.
3. Martinez-Zapien et al., Nature, 2016, 529(7587): p. 541-5.
4. Hall and Alexander, J Viral, 2003, 77(10): p. 6066-9.
5. Vaupel et al., Antioxid Redox Signal, 2007, 9(8): p. 1221-35.
6. Vaupel and Mayer, Cancer Metastasis Rev, 2007, 26(2): p. 225-39.
7. Hoppe-Seyler et al., Proceedings of the National Academy of Sciences, 2017, 114(6): p. E990-E998.
8. Overgaard J Clin Oncol, 2007, 25(26): p. 4066-74.
9. Hili et al., Sem ln Radial Oncol, 2015, 25(4):p. 260-72.
10. Manoochehri Khoshinani et al., Cancer Invest, 2016, 34(10): p. 536-545.
11. Torti and Torti, Nat Rev Cancer, 2013, 13(5): p. 342-55.
12. Sanvisens et al. Biomed J, 2013, 36(2): p. 51-8.
13. Waris and Ahsan, Journal of Carcinogenesis, 2006, 5: p. 14-14.
14. Shen and Huang, Curr Pharm Des, 2016, 22(28): p. 4443-50.
15. Zhou et al., Journal international du cancer, 2010, 127(10): p. 2467-2477.
16. Eberhard et al., Blood, 2009, 114(14): p. 3064-3073.
17. Clement et al., Int J. Cancer, 100: 491-498, 2002
18. Song et al., Cancer Res. 71: 7628-7639, 2011
19. Laberge et al., Nat. Cell Biol. 17: 1049-1061

The invention claimed is:

1. A method for treating cancer in a subject comprising contacting hypoxic cancer cells in the subject with a pharmaceutically compatible iron chelator or a prodrug thereof, wherein the subject is suspected or known to comprise hypoxic cancer cells, wherein the pharmaceutically compatible iron chelator or prodrug thereof comprises a structure (I)

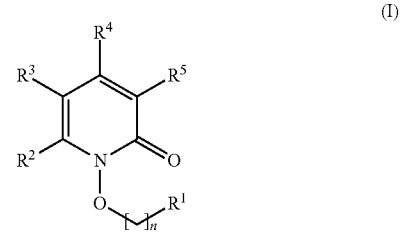

wherein:
n is 0, 1, 2, 3, 4, 5, or 6;
$R^1$ is H, optionally substituted carbonyl, optionally substituted phosphoryl, or optionally substituted sulfonyl;
$R^2$ is selected from cyclohexyl, —H, C1-C6 alkyl, C5-C8 cycloalkyl, C1-C6 alkoxy, and halogen;
$R^4$ is selected from methyl, —H, C1-C6 alkyl, C5-C8 cycloalkyl, C1-C6 alkoxy, and halogen; and
$R^3$ and $R^5$ are independently selected from —H, C1-C6 alkyl, C5-C8 cycloalkyl, C1-C6 alkoxy, and halogen.

2. The method of claim 1, wherein the pharmaceutically compatible iron chelator is ciclopirox (2(1H)-Pyridinone, 6-cyclohexyl-1-hydroxy-4-methylpyridin-2(1H)-one) or ciclopirox olamine.

3. The method of claim 1, wherein the hypoxic cancer cells are slowly proliferating or non-dividing hypoxic cancer cells.

4. The method of claim 3, wherein the hypoxic cancer cells are cancer cells under an oxygen saturation of at most about 5%, at most about 3%, or at most about 1%.

5. The method of claim 1, wherein the cancer forms at least one tumor mass having a diameter of at least about 1 mm, at least about 5 mm, or at least about 10 mm.

6. The method of claim 1, wherein the treating comprises administration of at least one further anticancer therapy, and optionally wherein the further anticancer therapy is radiotherapy, chemotherapy, anti-hormone therapy, targeted therapy, immunotherapy, or any combination thereof.

7. A method for inducing an irreversible proliferation arrest in hypoxic cancer cells comprising:
(a) contacting the hypoxic cancer cells with an iron chelator or prodrug thereof and, thereby,
(b) inducing an irreversible proliferation arrest in the hypoxic cancer cells, wherein the iron chelator or prodrug thereof comprises a structure (I)

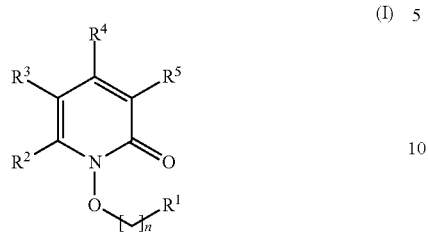

wherein:
n is 0, 1, 2, 3, 4, 5, or 6;
$R^1$ is H, optionally substituted carbonyl, optionally substituted phosphoryl, or optionally substituted sulfonyl;
$R^2$ is selected from cyclohexyl, —H, C1-C6 alkyl, C5-C8 cycloalkyl, C1-C6 alkoxy, and halogen;
$R^4$ is selected from methyl, —H, C1-C6 alkyl, C5-C8 cycloalkyl, C1-C6 alkoxy, and halogen; and
$R^3$ and $R^5$ are independently selected from —H, C1-C6 alkyl, C5-C8 cycloalkyl, C1-C6 alkoxy, and halogen.

8. The method of claim 7, wherein the pharmaceutically compatible iron chelator is ciclopirox (2(1H)-Pyridinone, 6-cyclohexyl-1-hydroxy-4-methylpyridin-2(1H)-one) or ciclopirox olamine.

9. The method of claim 1, wherein the cancer is a solid cancer, a metastasis, or a relapse thereof.

* * * * *